(12) United States Patent
Colborn

(10) Patent No.: US 9,402,550 B2
(45) Date of Patent: Aug. 2, 2016

(54) DYNAMIC HEART RATE THRESHOLD FOR NEUROLOGICAL EVENT DETECTION

(75) Inventor: John C Colborn, League City, TX (US)

(73) Assignee: CYBERTRONICS, INC., Houston, TX (US)

( * ) Notice: Subject to any disclaimer, the term of this patent is extended or adjusted under 35 U.S.C. 154(b) by 712 days.

(21) Appl. No.: 13/097,439

(22) Filed: Apr. 29, 2011

(65) Prior Publication Data

US 2012/0277605 A1 Nov. 1, 2012

(51) Int. Cl.
| A61B 5/02 | (2006.01) |
| A61B 5/024 | (2006.01) |
| A61B 5/0476 | (2006.01) |
| A61B 5/00 | (2006.01) |

(52) U.S. Cl.
CPC . *A61B 5/024* (2013.01); *A61B 5/02* (2013.01); *A61B 5/0476* (2013.01); *A61B 5/7275* (2013.01)

(58) Field of Classification Search
CPC ...... A61B 5/024; A61B 5/02405; A61B 5/02; A61B 5/0476; A61B 5/4094; A61B 5/7275
USPC .................................... 600/544, 508; 607/45
See application file for complete search history.

(56) References Cited

U.S. PATENT DOCUMENTS

| 4,172,459 A | 10/1979 | Hepp |
| 4,197,856 A | 4/1980 | Northrop |
| 4,291,699 A | 9/1981 | Geddes et al. |
| 4,320,766 A | 3/1982 | Alihanka et al. |
| 4,541,432 A | 9/1985 | Molina-Negro et al. |
| 4,573,481 A | 3/1986 | Bullara |
| 4,702,254 A | 10/1987 | Zabara |
| 4,867,164 A | 9/1989 | Zabara |
| 4,920,979 A | 5/1990 | Bullara |
| 4,949,721 A | 8/1990 | Toriu et al. |
| 4,979,511 A | 12/1990 | Terry, Jr. |

(Continued)

FOREIGN PATENT DOCUMENTS

| EP | 1145736 | 10/2001 |
| EP | 1486232 | 12/2004 |

(Continued)

OTHER PUBLICATIONS

Van Elmpt et al, "A Model of Heart rate Changes to Detect Seizures in Severe Epilepsy," Seizure, Bailliere Tindall, London, GB, vol. 15 No. 6, Sep. 1, 2006, pp. 366-375.

(Continued)

*Primary Examiner* — Michael Kahelin
*Assistant Examiner* — Minh Duc Pham
(74) *Attorney, Agent, or Firm* — Foley & Lardner LLP

(57) ABSTRACT

A method may include sensing a time of beat sequence of a patient's heart and processing said time of beat sequence with a medical device to identify a change in heart rate of a patient from a first heart rate to a second heart rate. The method may continue by determining with the medical device at least one of a) a ratio of the second heart rate to the first heart rate and b) a difference between the second heart rate and the first heart rate. The method may include determining with the medical device at least one of a) a dynamic ratio threshold for the ratio and b) a dynamic difference threshold for the difference, wherein the at least one threshold is based upon the first heart rate. The ratio and/or the difference may be compared to the threshold(s) to detect a neurological event, for example, an epileptic seizure.

15 Claims, 6 Drawing Sheets

(56) References Cited

U.S. PATENT DOCUMENTS

| | | |
|---|---|---|
| 5,025,807 A | 6/1991 | Zabara |
| 5,062,169 A | 11/1991 | Kennedy et al. |
| 5,113,869 A | 5/1992 | Nappholz et al. |
| 5,137,020 A | 8/1992 | Wayne et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,194,847 A | 3/1993 | Taylor et al. |
| 5,203,326 A | 4/1993 | Collins |
| 5,205,285 A | 4/1993 | Baker, Jr. |
| 5,213,568 A | 5/1993 | Lattin et al. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,243,980 A | 9/1993 | Mehra |
| 5,251,634 A | 10/1993 | Weinberg |
| 5,263,480 A | 11/1993 | Wernicke et al. |
| 5,269,302 A | 12/1993 | Swartz et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,313,953 A | 5/1994 | Yomtov et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,404,877 A | 4/1995 | Nolan et al. |
| 5,425,373 A | 6/1995 | Causey, III |
| 5,513,649 A | 5/1996 | Gevins et al. |
| 5,522,862 A | 6/1996 | Testerman et al. |
| 5,523,742 A | 6/1996 | Simkins et al. |
| 5,540,730 A | 7/1996 | Terry, Jr. et al. |
| 5,540,734 A | 7/1996 | Zabara |
| 5,571,150 A | 11/1996 | Wernicke et al. |
| 5,610,590 A | 3/1997 | Johnson et al. |
| 5,611,350 A | 3/1997 | John |
| 5,626,140 A | 5/1997 | Feldman et al. |
| 5,645,077 A | 7/1997 | Foxlin |
| 5,645,570 A | 7/1997 | Corbucci |
| 5,651,378 A | 7/1997 | Matheny et al. |
| 5,658,318 A | 8/1997 | Stroetmann et al. |
| 5,683,422 A | 11/1997 | Rise et al. |
| 5,690,681 A | 11/1997 | Geddes et al. |
| 5,690,688 A | 11/1997 | Noren et al. |
| 5,700,282 A | 12/1997 | Zabara |
| 5,707,400 A | 1/1998 | Terry, Jr. et al. |
| 5,713,926 A | 2/1998 | Hauser et al. |
| 5,716,377 A | 2/1998 | Rise et al. |
| 5,720,771 A | 2/1998 | Snell |
| 5,738,104 A | 4/1998 | Lo et al. |
| 5,743,860 A | 4/1998 | Hively et al. |
| 5,748,113 A | 5/1998 | Torch |
| 5,792,186 A | 8/1998 | Rise |
| 5,800,474 A | 9/1998 | Benabid et al. |
| 5,807,284 A | 9/1998 | Foxlin |
| 5,808,552 A | 9/1998 | Wiley et al. |
| 5,833,709 A | 11/1998 | Rise et al. |
| 5,853,005 A | 12/1998 | Scanlon et al. |
| 5,879,309 A | 3/1999 | Johnson et al. |
| 5,905,436 A | 5/1999 | Dwight et al. |
| 5,913,876 A | 6/1999 | Taylor et al. |
| 5,916,181 A | 6/1999 | Socci et al. |
| 5,916,239 A | 6/1999 | Geddes et al. |
| 5,928,272 A * | 7/1999 | Adkins et al. ................... 607/45 |
| 5,941,906 A | 8/1999 | Barreras, Sr. et al. |
| 5,942,979 A | 8/1999 | Luppino |
| 5,978,702 A | 11/1999 | Ward et al. |
| 5,978,972 A | 11/1999 | Stewart et al. |
| 5,987,352 A | 11/1999 | Klein et al. |
| 5,995,868 A | 11/1999 | Dorfmeister et al. |
| 6,016,449 A | 1/2000 | Fischell et al. |
| 6,018,682 A | 1/2000 | Rise |
| 6,048,324 A | 4/2000 | Socci et al. |
| 6,061,593 A | 5/2000 | Fischell et al. |
| 6,073,048 A | 6/2000 | Kieval et al. |
| 6,083,249 A | 7/2000 | Familoni |
| 6,091,992 A | 7/2000 | Bourgeois et al. |
| 6,095,991 A | 8/2000 | Krausman et al. |
| 6,104,956 A | 8/2000 | Naritoku et al. |
| 6,115,628 A | 9/2000 | Stadler et al. |
| 6,115,630 A | 9/2000 | Stadler et al. |
| 6,128,538 A | 10/2000 | Fischell et al. |
| 6,134,474 A | 10/2000 | Fischell et al. |
| 6,162,191 A | 12/2000 | Foxlin |
| 6,163,281 A | 12/2000 | Torch |
| 6,167,311 A | 12/2000 | Rezai |
| 6,171,239 B1 | 1/2001 | Humphrey |
| 6,175,764 B1 | 1/2001 | Loeb et al. |
| 6,205,359 B1 | 3/2001 | Boveja |
| 6,208,894 B1 | 3/2001 | Schulman et al. |
| 6,208,902 B1 | 3/2001 | Boveja |
| 6,221,908 B1 | 4/2001 | Kilgard et al. |
| 6,246,344 B1 | 6/2001 | Torch |
| 6,248,080 B1 | 6/2001 | Miesel et al. |
| 6,253,109 B1 | 6/2001 | Gielen |
| 6,269,270 B1 | 7/2001 | Boveja |
| 6,272,379 B1 | 8/2001 | Fischell et al. |
| 6,304,775 B1 | 10/2001 | Iasemidis et al. |
| 6,315,740 B1 | 11/2001 | Singh |
| 6,324,421 B1 | 11/2001 | Stadler et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,784 B1 | 3/2002 | Lozano et al. |
| 6,356,788 B2 | 3/2002 | Boveja |
| 6,361,507 B1 | 3/2002 | Foxlin |
| 6,361,508 B1 | 3/2002 | Johnson et al. |
| 6,366,813 B1 | 4/2002 | DiLorenzo |
| 6,366,814 B1 | 4/2002 | Boveja |
| 6,374,140 B1 | 4/2002 | Rise |
| 6,397,100 B2 | 5/2002 | Stadler et al. |
| 6,427,086 B1 | 7/2002 | Fischell et al. |
| 6,429,217 B1 | 8/2002 | Puskas |
| 6,441,731 B1 | 8/2002 | Hess |
| 6,449,512 B1 | 9/2002 | Boveja |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,501,983 B1 | 12/2002 | Natarajan et al. |
| 6,505,074 B2 | 1/2003 | Boveja et al. |
| 6,532,388 B1 | 3/2003 | Hill et al. |
| 6,539,263 B1 | 3/2003 | Schiff et al. |
| 6,542,081 B2 | 4/2003 | Torch |
| 6,542,774 B2 | 4/2003 | Hill et al. |
| 6,549,804 B1 | 4/2003 | Osorio et al. |
| 6,556,868 B2 | 4/2003 | Naritoku et al. |
| 6,560,486 B1 | 5/2003 | Osorio et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,594,524 B2 | 7/2003 | Esteller et al. |
| 6,599,250 B2 | 7/2003 | Webb et al. |
| 6,609,025 B2 | 8/2003 | Barrett et al. |
| 6,610,713 B2 | 8/2003 | Tracey |
| 6,611,715 B1 | 8/2003 | Boveja |
| 6,611,783 B2 | 8/2003 | Kelly, Jr. et al. |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,985 B2 | 9/2003 | Sweeney et al. |
| 6,628,987 B1 | 9/2003 | Hill et al. |
| 6,629,990 B2 | 10/2003 | Putz et al. |

(56) References Cited

U.S. PATENT DOCUMENTS

| | | |
|---|---|---|
| 6,647,296 B2 | 11/2003 | Fischell et al. |
| 6,656,125 B2 | 12/2003 | Misczynski et al. |
| 6,656,960 B2 | 12/2003 | Puskas |
| 6,668,191 B1 | 12/2003 | Boveja |
| 6,671,555 B2 | 12/2003 | Gielen et al. |
| 6,671,556 B2 | 12/2003 | Osorio et al. |
| 6,684,105 B2 | 1/2004 | Cohen et al. |
| 6,721,603 B2 | 4/2004 | Zabara et al. |
| 6,730,047 B2 | 5/2004 | Socci et al. |
| 6,735,474 B1 | 5/2004 | Loeb et al. |
| 6,738,671 B2 | 5/2004 | Christophersom et al. |
| 6,760,626 B1 | 7/2004 | Boveja |
| 6,763,256 B2 | 7/2004 | Kimball et al. |
| 6,768,968 B2 | 7/2004 | Ignatowski et al. |
| 6,768,969 B1 | 7/2004 | Nikitin et al. |
| 6,786,877 B2 | 9/2004 | Foxlin |
| 6,788,975 B1 | 9/2004 | Whitehurst et al. |
| 6,793,670 B2 | 9/2004 | Osorio et al. |
| 6,819,953 B2 | 11/2004 | Yonce et al. |
| 6,819,956 B2 | 11/2004 | DiLorenzo |
| 6,832,114 B1 | 12/2004 | Whitehurst et al. |
| 6,836,685 B1 | 12/2004 | Fitz |
| 6,850,601 B2 | 2/2005 | Jones et al. |
| 6,879,850 B2 | 4/2005 | Kimball |
| 6,885,888 B2 | 4/2005 | Rezai |
| 6,904,390 B2 | 6/2005 | Nikitin et al. |
| 6,920,357 B2 | 7/2005 | Osorio et al. |
| 6,923,784 B2 | 8/2005 | Stein |
| 6,931,274 B2 | 8/2005 | Williams et al. |
| 6,934,580 B1 | 8/2005 | Osorio et al. |
| 6,934,585 B1 | 8/2005 | Schloss |
| 6,944,501 B1 | 9/2005 | Pless |
| 6,957,107 B2 | 10/2005 | Rogers |
| 6,961,618 B2 | 11/2005 | Osorio et al. |
| 6,984,993 B2 | 1/2006 | Ariav |
| 6,985,771 B2 | 1/2006 | Fischell et al. |
| 6,990,377 B2 | 1/2006 | Gliner et al. |
| 7,006,859 B1 | 2/2006 | Osorio et al. |
| 7,006,872 B2 | 2/2006 | Gielen et al. |
| 7,010,351 B2 | 3/2006 | Firlik et al. |
| 7,024,247 B2 | 4/2006 | Gliner et al. |
| 7,035,684 B2 | 4/2006 | Lee |
| 7,054,792 B2 | 5/2006 | Frei et al. |
| 7,058,453 B2 | 6/2006 | Nelson et al. |
| 7,068,842 B2 | 6/2006 | Liang et al. |
| 7,076,288 B2 | 7/2006 | Skinner |
| 7,077,810 B2 | 7/2006 | Lange et al. |
| 7,079,977 B2 | 7/2006 | Osorio et al. |
| 7,104,947 B2 | 9/2006 | Riehl et al. |
| 7,110,820 B2 | 9/2006 | Tcheng et al. |
| 7,112,319 B2 | 9/2006 | Broderick et al. |
| 7,127,370 B2 | 10/2006 | Kelly et al. |
| 7,134,996 B2 | 11/2006 | Bardy |
| 7,139,677 B2 | 11/2006 | Hively et al. |
| 7,146,211 B2 | 12/2006 | Frei et al. |
| 7,146,217 B2 | 12/2006 | Firlik et al. |
| 7,146,218 B2 | 12/2006 | Esteller et al. |
| 7,149,572 B2 | 12/2006 | Frei et al. |
| 7,164,941 B2 | 1/2007 | Misczynski et al. |
| 7,167,743 B2 | 1/2007 | Heruth et al. |
| 7,167,750 B2 | 1/2007 | Knudson et al. |
| 7,174,206 B2 | 2/2007 | Frei et al. |
| 7,177,678 B1 | 2/2007 | Osorio et al. |
| 7,188,053 B2 | 3/2007 | Nikitin et al. |
| RE39,539 E | 4/2007 | Torch |
| 7,204,833 B1 | 4/2007 | Osorio et al. |
| 7,209,786 B2 | 4/2007 | Brockway |
| 7,209,787 B2 | 4/2007 | DiLorenzo |
| 7,221,981 B2 | 5/2007 | Gliner |
| 7,228,167 B2 | 6/2007 | Kara |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,254,439 B2 | 8/2007 | Misczynski et al. |
| 7,263,467 B2 | 8/2007 | Sackellares et al. |
| 7,274,298 B2 | 9/2007 | Frank |
| 7,277,758 B2 | 10/2007 | DiLorenzo |
| 7,280,867 B2 | 10/2007 | Frei et al. |
| 7,282,030 B2 | 10/2007 | Frei et al. |
| 7,289,844 B2 | 10/2007 | Misczynski et al. |
| 7,292,890 B2 | 11/2007 | Whitehurst et al. |
| 7,295,881 B2 | 11/2007 | Cohen et al. |
| 7,299,096 B2 | 11/2007 | Balzer et al. |
| 7,302,298 B2 | 11/2007 | Lowry et al. |
| 7,304,580 B2 | 12/2007 | Sullivan et al. |
| 7,305,268 B2 | 12/2007 | Gliner et al. |
| 7,313,440 B2 | 12/2007 | Miesel |
| 7,314,451 B2 | 1/2008 | Halperin et al. |
| 7,321,837 B2 | 1/2008 | Osorio et al. |
| 7,324,850 B2 | 1/2008 | Persen et al. |
| 7,324,851 B1 | 1/2008 | DiLorenzo |
| 7,330,760 B2 | 2/2008 | Heruth et al. |
| 7,346,391 B1 | 3/2008 | Osorio et al. |
| 7,353,063 B2 | 4/2008 | Simms, Jr. |
| 7,353,064 B2 | 4/2008 | Gliner et al. |
| 7,373,199 B2 | 5/2008 | Sackellares et al. |
| 7,385,443 B1 | 6/2008 | Denison |
| 7,389,144 B1 | 6/2008 | Osorio et al. |
| 7,389,147 B2 | 6/2008 | Wahlstrand et al. |
| 7,395,113 B2 | 7/2008 | Heruth et al. |
| 7,401,008 B2 | 7/2008 | Frei et al. |
| 7,403,820 B2 | 7/2008 | DiLorenzo |
| 7,420,472 B2 | 9/2008 | Tran |
| 7,433,732 B1 | 10/2008 | Carney et al. |
| 7,447,545 B2 | 11/2008 | Heruth et al. |
| 7,454,245 B2 | 11/2008 | Armstrong et al. |
| 7,488,293 B2 | 2/2009 | Marcovecchio et al. |
| 7,488,294 B2 | 2/2009 | Torch |
| 7,491,181 B2 | 2/2009 | Heruth et al. |
| 7,494,464 B2 | 2/2009 | Rzesnitzek et al. |
| 7,502,643 B2 | 3/2009 | Farringdon et al. |
| 7,515,054 B2 | 4/2009 | Torch |
| 7,539,532 B2 | 5/2009 | Tran |
| 7,539,533 B2 | 5/2009 | Tran |
| 7,539,543 B2 | 5/2009 | Schiff et al. |
| 7,558,622 B2 | 7/2009 | Tran |
| 7,565,132 B2 | 7/2009 | Ben |
| 7,590,453 B2 | 9/2009 | Heruth et al. |
| 7,620,456 B2 | 11/2009 | Gliner et al. |
| 7,629,890 B2 | 12/2009 | Sullivan et al. |
| 7,643,655 B2 | 1/2010 | Liang et al. |
| 7,647,121 B2 | 1/2010 | Wahlstrand et al. |
| 7,658,112 B2 | 2/2010 | Nakamura |
| 7,666,151 B2 | 2/2010 | Sullivan et al. |
| 7,714,757 B2 | 5/2010 | Denison et al. |
| 7,717,848 B2 | 5/2010 | Heruth et al. |
| RE41,376 E | 6/2010 | Torch |
| 7,733,224 B2 | 6/2010 | Tran |
| 7,747,318 B2 | 6/2010 | John et al. |
| 7,769,464 B2 | 8/2010 | Gerber et al. |
| 7,775,993 B2 | 8/2010 | Heruth et al. |
| 7,792,583 B2 | 9/2010 | Miesel et al. |
| 7,801,603 B2 | 9/2010 | Westlund et al. |
| 7,801,618 B2 | 9/2010 | Pless |
| 7,801,743 B2 | 9/2010 | Graves et al. |
| 7,813,802 B2 | 10/2010 | Tcheng et al. |
| 7,822,481 B2 | 10/2010 | Gerber et al. |
| 7,827,011 B2 | 11/2010 | DeVaul et al. |
| 7,831,305 B2 | 11/2010 | Gliner |
| 7,847,628 B2 | 12/2010 | Denison |
| 7,866,212 B2 | 1/2011 | Ariav et al. |
| 7,899,545 B2 | 3/2011 | John |
| 7,935,076 B2 | 5/2011 | Estes et al. |
| RE42,471 E | 6/2011 | Torch |
| 7,957,809 B2 | 6/2011 | Bourget et al. |
| 7,965,833 B2 | 6/2011 | Meir et al. |
| 7,974,671 B2 | 7/2011 | Fujiwara et al. |
| 7,996,076 B2 | 8/2011 | Burns et al. |
| 7,999,857 B2 | 8/2011 | Bunn et al. |
| 8,000,789 B2 | 8/2011 | Denison et al. |
| 8,000,794 B2 | 8/2011 | Lozano |
| 8,021,299 B2 | 9/2011 | Miesel et al. |

(56) References Cited

U.S. PATENT DOCUMENTS

| | | |
|---|---|---|
| 8,027,730 B2 | 9/2011 | John et al. |
| 8,027,737 B2 | 9/2011 | Kokones et al. |
| 8,075,499 B2 | 12/2011 | Nathan et al. |
| 8,109,891 B2 | 2/2012 | Kramer et al. |
| 8,649,871 B2 | 2/2014 | Frei et al. |
| 8,831,732 B2 | 9/2014 | Frei et al. |
| 2001/0032059 A1 | 10/2001 | Kelly et al. |
| 2002/0072782 A1 | 6/2002 | Osorio et al. |
| 2002/0099417 A1 | 7/2002 | Naritoku et al. |
| 2002/0116030 A1 | 8/2002 | Rezai |
| 2002/0151939 A1 | 10/2002 | Rezai |
| 2002/0188214 A1 | 12/2002 | Misczynski et al. |
| 2003/0040680 A1 | 2/2003 | Hassert et al. |
| 2003/0074032 A1 | 4/2003 | Gliner |
| 2003/0083716 A1 | 5/2003 | Nicolelis et al. |
| 2003/0083726 A1 | 5/2003 | Zeijlemaker et al. |
| 2003/0125786 A1 | 7/2003 | Gliner et al. |
| 2003/0130706 A1 | 7/2003 | Sheffield et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0195588 A1 | 10/2003 | Upton et al. |
| 2003/0208212 A1 | 11/2003 | Cigaina |
| 2003/0210147 A1 | 11/2003 | Humbard |
| 2003/0212440 A1 | 11/2003 | Boveja |
| 2003/0236474 A1 | 12/2003 | Singh |
| 2003/0236558 A1 | 12/2003 | Whitehurst et al. |
| 2004/0006278 A1 | 1/2004 | Webb et al. |
| 2004/0030365 A1 | 2/2004 | Rubin et al. |
| 2004/0088024 A1 | 5/2004 | Firlik et al. |
| 2004/0111045 A1 | 6/2004 | Sullivan et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138647 A1 | 7/2004 | Osorio et al. |
| 2004/0138711 A1 | 7/2004 | Osorio et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0172085 A1 | 9/2004 | Knudson et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0199212 A1 | 10/2004 | Fischell et al. |
| 2004/0225335 A1 | 11/2004 | Whitehurst et al. |
| 2004/0249302 A1 | 12/2004 | Donoghue et al. |
| 2004/0249416 A1 | 12/2004 | Yun et al. |
| 2005/0004621 A1 | 1/2005 | Boveja et al. |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0022606 A1 | 2/2005 | Partin et al. |
| 2005/0027284 A1 | 2/2005 | Lozano et al. |
| 2005/0033378 A1 | 2/2005 | Sheffield et al. |
| 2005/0033379 A1 | 2/2005 | Lozano et al. |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060001 A1 | 3/2005 | Singhal et al. |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075701 A1 | 4/2005 | Shafer |
| 2005/0075702 A1 | 4/2005 | Shafer |
| 2005/0101873 A1 | 5/2005 | Misczynski et al. |
| 2005/0107716 A1 | 5/2005 | Eaton et al. |
| 2005/0119703 A1 | 6/2005 | DiLorenzo |
| 2005/0119711 A1* | 6/2005 | Cho et al. .................. 607/42 |
| 2005/0124901 A1 | 6/2005 | Misczynski et al. |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0143786 A1 | 6/2005 | Boveja et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0187590 A1 | 8/2005 | Boveja et al. |
| 2005/0192644 A1 | 9/2005 | Boveja et al. |
| 2005/0197590 A1 | 9/2005 | Osorio et al. |
| 2005/0203366 A1 | 9/2005 | Donoghue et al. |
| 2005/0245971 A1 | 11/2005 | Brockway et al. |
| 2005/0261542 A1 | 11/2005 | Riehl |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0288600 A1 | 12/2005 | Zhang et al. |
| 2005/0288760 A1 | 12/2005 | Machado et al. |
| 2006/0009815 A1 | 1/2006 | Boveja |
| 2006/0018833 A1 | 1/2006 | Murphy et al. |
| 2006/0030892 A1 | 2/2006 | Kadhiresan et al. |
| 2006/0074450 A1 | 4/2006 | Boveja |
| 2006/0079936 A1 | 4/2006 | Boveja |
| 2006/0094971 A1 | 5/2006 | Drew |
| 2006/0095081 A1 | 5/2006 | Zhou et al. |
| 2006/0106430 A1 | 5/2006 | Fowler et al. |
| 2006/0135877 A1 | 6/2006 | Giftakis et al. |
| 2006/0135881 A1 | 6/2006 | Giftakis et al. |
| 2006/0149139 A1 | 7/2006 | Bonmassar et al. |
| 2006/0155495 A1 | 7/2006 | Osorio et al. |
| 2006/0161208 A1 | 7/2006 | Pastore et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0212097 A1 | 9/2006 | Varadan et al. |
| 2006/0224067 A1 | 10/2006 | Giftakis et al. |
| 2006/0224191 A1 | 10/2006 | DiLorenzo |
| 2006/0241697 A1 | 10/2006 | Libbus et al. |
| 2006/0241725 A1 | 10/2006 | Libbus et al. |
| 2006/0293720 A1 | 12/2006 | DiLorenzo |
| 2007/0027486 A1 | 2/2007 | Armstrong et al. |
| 2007/0027497 A1 | 2/2007 | Parnis et al. |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0043392 A1 | 2/2007 | Gliner et al. |
| 2007/0055320 A1 | 3/2007 | Weinand et al. |
| 2007/0073150 A1 | 3/2007 | Gopalsami et al. |
| 2007/0073355 A1 | 3/2007 | DiLorenzo |
| 2007/0088403 A1 | 4/2007 | Wyler et al. |
| 2007/0100278 A1 | 5/2007 | Frei et al. |
| 2007/0100392 A1 | 5/2007 | Maschino et al. |
| 2007/0142862 A1 | 6/2007 | DiLorenzo |
| 2007/0142873 A1 | 6/2007 | Esteller et al. |
| 2007/0150024 A1 | 6/2007 | Leyde et al. |
| 2007/0150025 A1 | 6/2007 | DiLorenzo et al. |
| 2007/0156031 A1 | 7/2007 | Sullivan et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0173902 A1 | 7/2007 | Maschino et al. |
| 2007/0179534 A1 | 8/2007 | Firlik et al. |
| 2007/0179557 A1 | 8/2007 | Maschino et al. |
| 2007/0179558 A1 | 8/2007 | Gliner et al. |
| 2007/0208212 A1 | 9/2007 | DiLorenzo |

(56) References Cited

U.S. PATENT DOCUMENTS

| | | |
|---|---|---|
| 2007/0213785 A1 | 9/2007 | Osorio et al. |
| 2007/0233192 A1 | 10/2007 | Craig |
| 2007/0238939 A1* | 10/2007 | Giftakis et al. ............... 600/301 |
| 2007/0239210 A1 | 10/2007 | Libbus et al. |
| 2007/0242661 A1 | 10/2007 | Tran et al. |
| 2007/0244407 A1 | 10/2007 | Osorio |
| 2007/0249953 A1 | 10/2007 | Osorio et al. |
| 2007/0249954 A1 | 10/2007 | Virag et al. |
| 2007/0249955 A1 | 10/2007 | Carlson et al. |
| 2007/0255147 A1 | 11/2007 | Drew et al. |
| 2007/0255155 A1 | 11/2007 | Drew et al. |
| 2007/0260147 A1 | 11/2007 | Giftakis et al. |
| 2007/0260289 A1 | 11/2007 | Giftakis et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2008/0004904 A1 | 1/2008 | Tran et al. |
| 2008/0033503 A1 | 2/2008 | Fowler et al. |
| 2008/0033508 A1 | 2/2008 | Frei et al. |
| 2008/0046035 A1 | 2/2008 | Fowler et al. |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081958 A1 | 4/2008 | Denison et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161706 A1 | 7/2008 | Cho et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0208013 A1 | 8/2008 | Zhang et al. |
| 2008/0208284 A1 | 8/2008 | Rezai et al. |
| 2008/0258907 A1 | 10/2008 | Kalpaxis et al. |
| 2008/0269579 A1 | 10/2008 | Schiebler et al. |
| 2008/0275327 A1 | 11/2008 | Faarbaek et al. |
| 2008/0275328 A1 | 11/2008 | Jones et al. |
| 2008/0275349 A1 | 11/2008 | Halperin et al. |
| 2008/0281376 A1 | 11/2008 | Gerber et al. |
| 2008/0281381 A1 | 11/2008 | Gerber et al. |
| 2008/0281550 A1 | 11/2008 | Hogle et al. |
| 2008/0319281 A1 | 12/2008 | Aarts et al. |
| 2009/0030345 A1 | 1/2009 | Bonnet et al. |
| 2009/0040052 A1 | 2/2009 | Cameron et al. |
| 2009/0054731 A1 | 2/2009 | Magar et al. |
| 2009/0054742 A1 | 2/2009 | Kaminska et al. |
| 2009/0060287 A1 | 3/2009 | Hyde et al. |
| 2009/0076350 A1 | 3/2009 | Bly et al. |
| 2009/0099624 A1 | 4/2009 | Kokones et al. |
| 2009/0099627 A1 | 4/2009 | Molnar et al. |
| 2009/0105785 A1 | 4/2009 | Wei et al. |
| 2009/0137921 A1 | 5/2009 | Kramer et al. |
| 2009/0227882 A1 | 9/2009 | Foo |
| 2009/0227888 A1 | 9/2009 | Salmi |
| 2009/0322540 A1 | 12/2009 | Richardson et al. |
| 2010/0010382 A1 | 1/2010 | Panken |
| 2010/0010392 A1 | 1/2010 | Skelton et al. |
| 2010/0010583 A1 | 1/2010 | Panken et al. |
| 2010/0023348 A1 | 1/2010 | Hardee et al. |
| 2010/0056878 A1 | 3/2010 | Partin et al. |
| 2010/0106217 A1 | 4/2010 | Colborn |
| 2010/0109875 A1 | 5/2010 | Ayon et al. |
| 2010/0121214 A1 | 5/2010 | Giftakis et al. |
| 2010/0217533 A1 | 8/2010 | Nadkarni et al. |
| 2010/0223020 A1 | 9/2010 | Goetz |
| 2010/0228103 A1 | 9/2010 | Schecter |
| 2010/0228314 A1 | 9/2010 | Goetz |
| 2010/0268056 A1 | 10/2010 | Picard et al. |
| 2010/0274146 A1 | 10/2010 | Li et al. |
| 2010/0274303 A1 | 10/2010 | Bukhman |
| 2010/0280336 A1 | 11/2010 | Giftakis et al. |
| 2010/0280578 A1 | 11/2010 | Skelton et al. |
| 2010/0280579 A1 | 11/2010 | Denison et al. |
| 2010/0286567 A1 | 11/2010 | Wolfe et al. |
| 2010/0298661 A1 | 11/2010 | Mccombie et al. |
| 2010/0298742 A1 | 11/2010 | Perlman et al. |
| 2010/0305665 A1 | 12/2010 | Miesel et al. |
| 2010/0312188 A1 | 12/2010 | Robertson et al. |
| 2011/0029044 A1 | 2/2011 | Hyde et al. |
| 2011/0040204 A1 | 2/2011 | Ivorra et al. |
| 2011/0040546 A1 | 2/2011 | Gerber et al. |
| 2011/0060252 A1 | 3/2011 | Simonsen et al. |
| 2011/0066062 A1 | 3/2011 | Banet et al. |
| 2011/0066081 A1 | 3/2011 | Goto et al. |
| 2011/0137372 A1 | 6/2011 | Makous et al. |
| 2011/0172545 A1 | 7/2011 | Grudic et al. |
| 2011/0230730 A1 | 9/2011 | Quigg et al. |
| 2011/0245629 A1 | 10/2011 | Giftakis et al. |
| 2011/0251469 A1 | 10/2011 | Varadan |
| 2011/0270096 A1* | 11/2011 | Osorio et al. ................. 600/483 |
| 2011/0270117 A1 | 11/2011 | Warwick et al. |
| 2011/0270134 A1 | 11/2011 | Skelton et al. |
| 2011/0295127 A1 | 12/2011 | Sandler et al. |
| 2011/0306846 A1 | 12/2011 | Osorio |
| 2011/0313484 A1 | 12/2011 | Hincapie et al. |

FOREIGN PATENT DOCUMENTS

| | | |
|---|---|---|
| EP | 2258444 | 12/2010 |
| EP | 1087815 | 3/2013 |
| GB | 2026870 | 2/1980 |
| GB | 2079610 | 1/1982 |
| WO | 93/02744 | 2/1993 |
| WO | 97/26823 | 7/1997 |
| WO | 00/64336 | 11/2000 |
| WO | 2004/036377 | 4/2004 |
| WO | 2005/007120 | 1/2005 |
| WO | 2005/053788 | 6/2005 |
| WO | 2005/067299 | 7/2005 |
| WO | 2006/050144 | 5/2006 |
| WO | 2006/122148 | 11/2006 |
| WO | 2007/066343 | 6/2007 |
| WO | 2007/072425 | 6/2007 |
| WO | 2007/124126 | 11/2007 |
| WO | 2007/124190 | 11/2007 |
| WO | 2007/124192 | 11/2007 |
| WO | 2007/142523 | 12/2007 |
| WO | 2008/045597 | 4/2008 |

OTHER PUBLICATIONS

International Search Report for PCT/US2011/061057 dated Feb. 7, 2012.

Bachman, D.,S. et al.; "*Effects of Vagal Volleys and Serotonin on Units of Cingulate Cortex in Monkeys*;" Brain Research, vol. 130 (1977). pp. 253-269.

Baevskii, R.M. "*Analysis of Heart Rate Variability in Space Medicine*;" Human Physiology, vol. 28, No. 2, (2002); pp. 202-213.

Baevsky, R.M., et al.; "*Autonomic Cardiovascular and Respiratory Control During Prolonged Spaceflights Aboard the International Space Station*;" J. Applied Physiological, vol. 103, (2007) pp. 156-161.

Boon, P., et al.; "*Vagus Nerve Stimulation for Epilepsy, Clinical Efficacy of Programmed and Magnet Stimulation*;" (2001); pp. 93-98.

Boon, Paul, et al.; "*Programmed and Magnet-Induced Vagus Nerve Stimulation for Refractory Epilepsy*;" Journal of Clinical Neurophysiology vol. 18 No. 5; (2001); pp. 402-407.

Borovikova, L.V., et al.; "*Vagus Nerve Stimulation Attenuates the Systemic Inflammatory Response to Endotoxin*;" Letters to Nature; vol. 405; (May 2000); pp. 458-462.

Brack, Kieran E., et al.; "*Interaction Between Direct Sympathetic and Vagus Nerve Stimulation on Heart Rate in the Isolated Rabbit Heart*;" Experimental Physiology Jan. 2004, vol. 89, No. 1; pp. 128-139.

(56) References Cited

OTHER PUBLICATIONS

Chakravarthy, N., et al.; "Controlling Synchronization in a Neuron-Level Population Model;" International Journal of Neural Systems, vol. 17, No. 2 (2007) pp. 123-138.

Clark, K.B., et al.; "Posttraining Electrical Stimulation of Vagal Afferents with Concomitant Vagal Efferent Inactivation Enhances Memory Storage Processes in the Rat;" Neurobiology of Learning and Memory, vol. 70, 364-373 (1998).

Elmpt, W.J.C., et al.; "A Model of Heart Rate Changes to Detect Seizures in Severe Epilepsy" Seizure vol. 15, (2006) pp. 366-375.

Frei, M.G., et al.; "Left Vagus Nerve Stimulation with the Neurocybernetic Prosthesis Has Complex Effects on Heart Rate and on Its Variability in Humans:" Epilepsia, vol. 42, No. 8 (2001); pp. 1007-1016.

George, M.S., et al.; "Vagus Nerve Stimulation: A New Tool for Brain Research and Therapy;" Society of Biological Psychiatry vol. 47 (2000) pp. 287-295.

"Heart Rate Variability—Standards of Measurement, Physiological Interpretation, and Clinical Use" Circulation—Electrophysiology vol. 93, No. 5; found at: http://circ.ahajournals.org/cgi/content-nw/full/93/5/1043/F3, Sep. 10, 2013.

Henry, Thomas R.; "Therapeutic Mechanisms of Vague Name Stimulation;". Neurology, vol. 59 (Supp 4) (Sep. 2002), pp. S3-S14.

Hallowitz et al., "Effects of Vagal Volleys on Units of Intralaminar and Juxtalaminar Thalamic Nuclei in Monkeys;" Brain Research, vol. 130 (1977), pp. 271-286.

Iasemidis; L.D., et al.; "Dynamical Resetting of the Human Brain at Epilepctic Seizures: Application of Nonlinear Dynamics and Global Optimization Techniques;" IEEE Transactions on Biomedical Engineering, vol. 51, No. 3 (Mar. 2004); pp. 493-506.

Iasemidis; L.D., et al.; "Spatiotemporal Transition to Epileptic Seizures: A Nonlinear Dynamical Analysis of Scalp and Intracranial EEG Recordings;" Spatiotemporal Models in Biological and Artificial Systems; F.L. Silva et al. (Eds.) IOS Press, 1997; pp. 81-88.

Iasemidis, L.D.; "Epileptic Seizure Prediction and Control" IEEE Transactions on Biomedical Engineering, vol. 50, No. 5 (May 2003); pp. 549-558.

Kautzner, J., et al.; "Utility of Short-Term Heart Rate Variability for Prediction of Sudden Cardiac Death After Acute Myocardial Infarction" Acta Univ. Palacki. Olomuc., Fac. Med., vol. 141 (1998) pp. 69-73.

Koenig, S.A., et al.; "Vagus Nerve Stimulation Improves Severely Impaired Heart Rate Variability in a Patient with Lennox-Gastaut-Syndrome" Seizure (2007) Article in Press—YSEIZ-1305; pp. 1-4.

Koo, B., "EEG Changes With Vagus Nerve Stimulation" Journal of Clinical Neurophysiology, vol. 18 No. 5 (Sep. 2001); pp. 434-441.

Krittayaphong, M.D., et al.; "Heart Rate Variability in Patients with Coronary Artery Disease: Differences in Patients with Higher and Lower Depression Scores" Psychosomatic Medicine vol. 59 (1997) pp. 231-235.

Leutmezer, F., et al.; "Electrocardiographic Changes at the Onset of Epileptic Seizures;" Epilepsia, vol. 44, No. 3; (2003); pp. 348-354.

Lewis, M.E., et al.; "Vagus Nerve Stimulation Decreases Left Ventricular Contractility in Vivo in the Human and Pig Heart" The Journal of Physiology vol. 534, No. 2, (2001) pp. 547-552.

Li, M., et al.; "Vagal Nerve Stimulation Markedly Improves Long-Term Survival After Chronic Heart Failure in Rats;" Circulation (Jan. 2004) pp. 120-124.

Licht, C.M.M.; Association Between Major Depressive Disorder and Heart Rate Variability in the Netherlands Study of Depression and Anxiety (NESDA); Arch. Gen Psychiatry, vol. 65, No. 12 (Dec. 2008); pp. 1358-1367.

Lockard et al., "Feasibility and Safety of Vagal Stimulation in Monkey Model;" Epilepsia, vol. 31 (Supp. 2) (1990), pp. S20-S26.

McClintock, P., "Can Noise Actually Boost Brain Power" Physics World Jul. 2002; pp. 20-21.

Mori, T., et al.; "Noise-Induced Entrainment and Stochastic Resonance in Human Brain Waves" Physical Review Letters vol. 88, No. 21 (2002); pp. 218101-1-218101-4.

Mormann, F., "Seizure prediction: the long and winding road," Brain 130 (2007), 314-333.

Nouri, M.D.; "Epilepsy and the Autonomic Nervous System" emedicine (updated May 5, 2006); pp. 1-14; http://www.emedicine.com/neuro/topic658.htm.

O'Regan, M.E., et al.; "Abnormalities in Cardiac and Respiratory Function Observed During Seizures in Childhood" Developmental Medicine & Child Neurlogy, vol. 47 (2005) pp. 4-9.

Pathwardhan, R.V., et al., Control of Refractory status epilepticus precipitated by anticonvulasnt withdrawal using left vagal nerve stimulation: a case report, Surgical Neurology 64 (2005) 170-73.

Poddubnaya, E.P., "Complex Estimation of Adaptation Abilities of the Organism in Children Using the Indices of Responsiveness of the Cardiovascular System and Characteristics of EEG" Neurophysiology vol. 38, No. 1 (2006); pp. 63-74.

Rugg-Gunn, F.J., et al.; "Cardiac Arrhythmias in Focal Epilepsy: a Prospective Long-Term Study" www.thelancet.com vol. 364 (2004) pp. 2212-2219.

Sajadieh, A., et al.; "Increased Heart Rate and Reduced Heart-Rte Variability are Associated with Subclinical Inflammation in Middle-Aged and Elderly Subjects with No Apparent Heart Disease" European Heart Journal vol. 25, (2004); pp. 363-370.

Schernthaner, C., et al.; "Autonomic Epilepsy—The Influence of Epileptic Discharges on Heart Rate and Rhythm" The Middle European Journal of Medicine vol. 111, No. 10 (1999) pp. 392-401.

Terry et al.; "The Implantable Neurocybernetic Prosthesis System", Pacing and Clinical Electrophysiology, vol. 14, No. 1 (Jan. 1991), pp. 86-93.

Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.

Umetani, M.D., et al.; "Twenty-Four Hour Time Domain Heart Rate Variability and Heart Rate: Relations to Age and Gender Over Nince Decades" JACC vol. 31, No. 3; (Mar. 1998); pp. 593-601.

Vonck, K., et al. "The Mechanism of Action of Vagus Nerve Stimulation for Refractory Epilepsy—The Current Status", Journal of Neurophysiology, vol. 18 No. 5 (2001), pp. 394-401.

Woodbury, et al., "Vagal Stimulation Reduces the Severity of Maximal Electroshock Seizures in Intact Rats. Use of a Cuff Electrode for Stimulating and Recording"; Pacing and Clinical Electrophysiology, vol. 14 (Jan. 1991), pp. 94-107.

Zabara, J.; "Neuroinhibition of Xylaine Induced Emesis" Pharmacology & Toxicology, vol. 63 (1988) pp. 70-74.

Zabara, J. "Inhibition of Experimental Seizures in Canines by Repetivie Vagal Stimulation" Epilepsia vol. 33, No. 6 (1992); pp. 1005-1012.

Zabara, J., et al.; "Neural Control of Circulation I" The Physiologist, vol. 28 No. 4 (1985); 1 page.

Zabara, J., et al.; "Neuroinhibition in the Regulation of Emesis" Space Life Sciences, vol. 3 (1972) pp. 282-292.

Osorio, Ivan et al., "An Introduction to Contingent (Closed-Loop) Brain Electrical Stimulation for Seizure Blockage, to Ultra-Short-Term Clinical Trials, and to Multidimensional Statistical Analysis of Therapeutic Efficacy," Journal of Clinical Neurophysiology, vol. 18, No. 6, pp. 533-544, 2001.

Osorio, Ivan et al., "Automated Seizure Abatement in Humans Using Electrical Stimulation," Annals of Neurology, vol. 57, No. 2, pp. 258-268, 2005.

Osorio et al., "Seizure Abatement with Single DC Pulses: Is Phase Resetting At Play?", IJNS vol. 19, No. 3 (2009), 15 pgs.

Sunderam, Sridhar et al., "Vagal and Sciatic Nerve Stimulation Have Complex, Time-Dependent Effects on Chemically-Induced Seizures: A Controlled Study," Brain Research, vol. 918, pp. 60-66, 2001.

Weil, Sabine et al, "Heart Rate Increase in Otherwise Subclinical Seizures Is Different in Temporal Versus Extratemporal Seizure Onset: Support for Temporal Lobe Automatic Influence," Epileptic Disord., vol. 7, No. 3, Sep. 2005, pp. 199-204.

Digenarro, Giancarlo et al., "Ictal Heart Rate Increase Precedes EEG Discharge in Drug-Resistant Mesial Temporal Lobe Seizures," Clinical Neurophysiology, No. 115, 2004, pp. 1169-1177.

(56) References Cited

OTHER PUBLICATIONS

Zijlmans, Maeike et al., "Heart Rate Changes and ECG Abnormalities During Epileptic Seizures: Prevalence and Definition of an Objective Clinical Sign," Epilepsia, vol. 43, No. 8, 2002, pp. 847-854.

O'Donovan, Cormac A. et al., "Computerized Seizure Detection Based on Heart Rate Changes," abstract of AES Proceedings, Epilepsia, vol. 36, Suppl. 4, 1995, p. 7.

Robinson, Stephen E et al., "Heart Rate Variability Changes As Predictor of Response to Vagal Nerve Stimulation Therapy for Epilepsy," abstract of AES Proceedings,Epilepsia, vol. 40, Suppl. 7, 1999, p. 147.

Hass, Shane M. et al., "Strategies for Adapting Automated Seizure Detection Alogrithms," Med Eng Phys, Oct. 2007; 29 (8); 895-909.

Long, Teresa J. et al., "Effectiveness of Heart Rate Seizure Detection Compared to EEG in an Epilepsy MoitoringUnit (EMU)," abstract of AES Proceedings, Epilepsia, vol. 40, Suppl. 7, 1999, p. 174.

\* cited by examiner

DYNAMIC HEART RATE THRESHOLD FOR NEUROLOGICAL EVENT DETECTION

TECHNICAL FIELD

The present invention relates generally to methods and devices for detection of medical events and, more particularly, to algorithms for detection of such medical events based at least in part on the heart rate of a patient. The medical event may be an epileptic seizure or an increased risk of an epileptic seizure.

BACKGROUND

Medical devices (MDs) have been used to detect events associated with a range of medical conditions. Upon a positive event detection, MDs may provide a range of responsive actions such as logging or recording, warning, providing treatment, or summoning assistance. MDs may be implantable, external, or may include both implantable and external components.

For epilepsy patients, MDs having seizure detection algorithms have been proposed. Detection may be based upon autonomic and/or neurologic data from the patient. Treatment therapies may be initiated in response to detection to prevent, terminate, or reduce the severity of seizures in patients with epilepsy, and may include, e.g., drug infusion via an implanted pump, and electrical stimulation therapies such as deep brain stimulation (DBS) or vagus nerve stimulation (VNS).

Electrical stimulation therapies applied in response to detection of a seizure is referred to as closed-loop stimulation. Open-loop stimulation, in contrast, the electrical signal is applied to the target tissue according to specified parameters for a defined period of time (e.g., 30 seconds), referred to as the on-time, after which the electrical signal ceases for a defined period of time (e.g., 5 minutes), referred to as the off-time. In addition to open-loop and closed-loop stimulation, some MDs allow stimulation to be initiated manually by a patient or caregiver (e.g., by a magnet signal provided transcutaneously to an IMD). Combinations of open-loop, closed-loop and manual stimulation may also be permitted.

Algorithms to detect epileptic seizures (or an increased risk of a seizure, either or both of which may constitute a "seizure event") have been proposed based upon one or more cardiac parameters such as heart rate or heart rate variability. See, e.g., U.S. Pat. No. 5,928,272, U.S. Pat. No. 6,341,236, U.S. Pat. No. 6,671,556, U.S. Pat. No. 6,961,618, U.S. Pat. No. 6,768,969, U.S. application Ser. No. 12/770,562, U.S. application Ser. No. 12/771,727, and U.S. application Ser. No. 12/771,783, which are hereby incorporated herein by reference. Current detection algorithms, however, have unacceptably high rates of false positive detections (i.e., detecting a seizure event when no seizure has occurred) and false negatives. There is a need for improved algorithms having both greater sensitivity (ability to detect seizures) and specificity (detecting only seizure events).

SUMMARY

In accordance with the present disclosure, the disadvantages and problems associated with prior cardiac-based seizure detection algorithms have been substantially reduced or eliminated.

In some embodiments, a method comprises sensing a time of beat sequence of a patient's heart and processing said time of beat sequence with a medical device to identify a change in heart rate of a patient from a first heart rate to a second heart rate. The method may continue by determining with the medical device at least one of a) a ratio of the second heart rate to the first heart rate and b) a difference between the second heart rate and the first heart rate. The method also comprises determining with the medical device at least one of a) a dynamic ratio threshold for the ratio and b) a dynamic difference threshold for the difference, wherein the at least one threshold is based upon the first heart rate. In one embodiment, the method may include comparing at least one of a) the ratio to the dynamic ratio threshold and b) the difference to the dynamic difference threshold. The method may also include detecting a neurologic event when at least one of a) the ratio exceeds the dynamic ratio threshold and b) the difference exceeds the dynamic difference threshold. In another embodiment, the method may include initiating at least one responsive action selected from logging at least one of the occurrence, time of occurrence, or a severity measure of the neurological event, issuing a warning of the neurological event, issuing an alarm, initiating a responsive therapy to treat the neurologic event, sending an email to at least one of the patient, a caregiver, a responder, and a physician.

In other embodiments, an article of manufacture may comprise a computer-readable storage medium having programming configured to cause processing circuitry to perform processing including the methods described herein.

In other embodiments, an apparatus comprises at least one sensor configured to sense a time of beat sequence of a patient's heart. The apparatus may further comprise a medical device having a heart rate determination module configured to identify from the time of beat sequence a change in heart rate of the patient from a first heart rate to a second heart rate. The medical device also includes a parameter determination module configured to determine at least one of 1) a ratio of the second heart rate to the first heart rate and 2) a difference between the second heart rate and the first heart rate. The medical device may also include a dynamic threshold determination module configured to determine at least one of 1) a dynamic ratio threshold for the ratio and 2) a dynamic difference threshold for the difference, wherein the at least one threshold is based upon the first heart rate. The medical device may additionally include a comparison module configured to compare at least one of 1) the ratio to the dynamic ratio threshold and 2) the difference to the dynamic difference threshold and a neurologic event detection module configured to detect a neurologic event when at least one of 1) the ratio exceeds the dynamic ratio threshold and 2) the difference exceeds the dynamic difference threshold The present disclosure provides various technical advantages. Various embodiments may have none, some, or all of these advantages. One advantage is that the disclosed medical device (MD) may be configured to determine a dynamic threshold for reducing errors in detecting seizure events. The MD may determine the dynamic threshold based at least in part on an activity level of the patient. When a typical person is engaged in a sedentary activity such as sleeping, merely standing up may cause a significant increase in heart rate. To avoid false positive and/or negative seizure event detections, the MD may be configured to determine when the patient is engaged in a sedentary activity. At such times, the MD may apply a relatively high dynamic threshold for indicating the occurrence of a seizure event.

The MD may be further configured to determine when a person is engaged in a strenuous activity. When a typical person is engaged in a strenuous activity such as running, a relatively high amount of additional effort is required to cause even a moderate increase in heart rate. To increase the responsiveness of the MD at such times, the MD may be configured to apply a relatively low dynamic threshold when the patient is engaged in a strenuous activity. Thus, the determination of the MD regarding detection of seizure events may be more accurate than in traditional medical devices.

Other advantages of the present disclosure will be readily apparent to one skilled in the art from the description and the appended claims.

BRIEF DESCRIPTION OF THE DRAWINGS

For a more complete understanding of the present disclosure and its advantages, reference is now made to the following description taken in conjunction with the accompanying drawings, in which.

DETAILED DESCRIPTION

Without being bound by theory, it is believed that one factor contributing to poor performance of existing seizure detection algorithms is the failure of existing algorithms to take into account the physical activity levels of the patient in distinguishing between seizure activity and non-seizure activity. For example, changes in heart rate when the patient is relatively inactive (e.g., sleeping, or awake but relatively inactive) may have a significantly different meaning in terms of whether a seizure event has occurred (and whether, e.g., an event should be logged and/or closed-loop stimulation should be initiated), compared to periods when the patient is active but not experiencing a seizure (e.g., climbing a flight of stairs or exercising). Because qualitative information indicative of the patient's precise physical activity level is generally unavailable, many proposed algorithms may either erroneously detect a seizure event (and log or initiate treatment) when there is no seizure, or may fail to detect a seizure when it occurs (a false negative), or both.

Figure 1A:
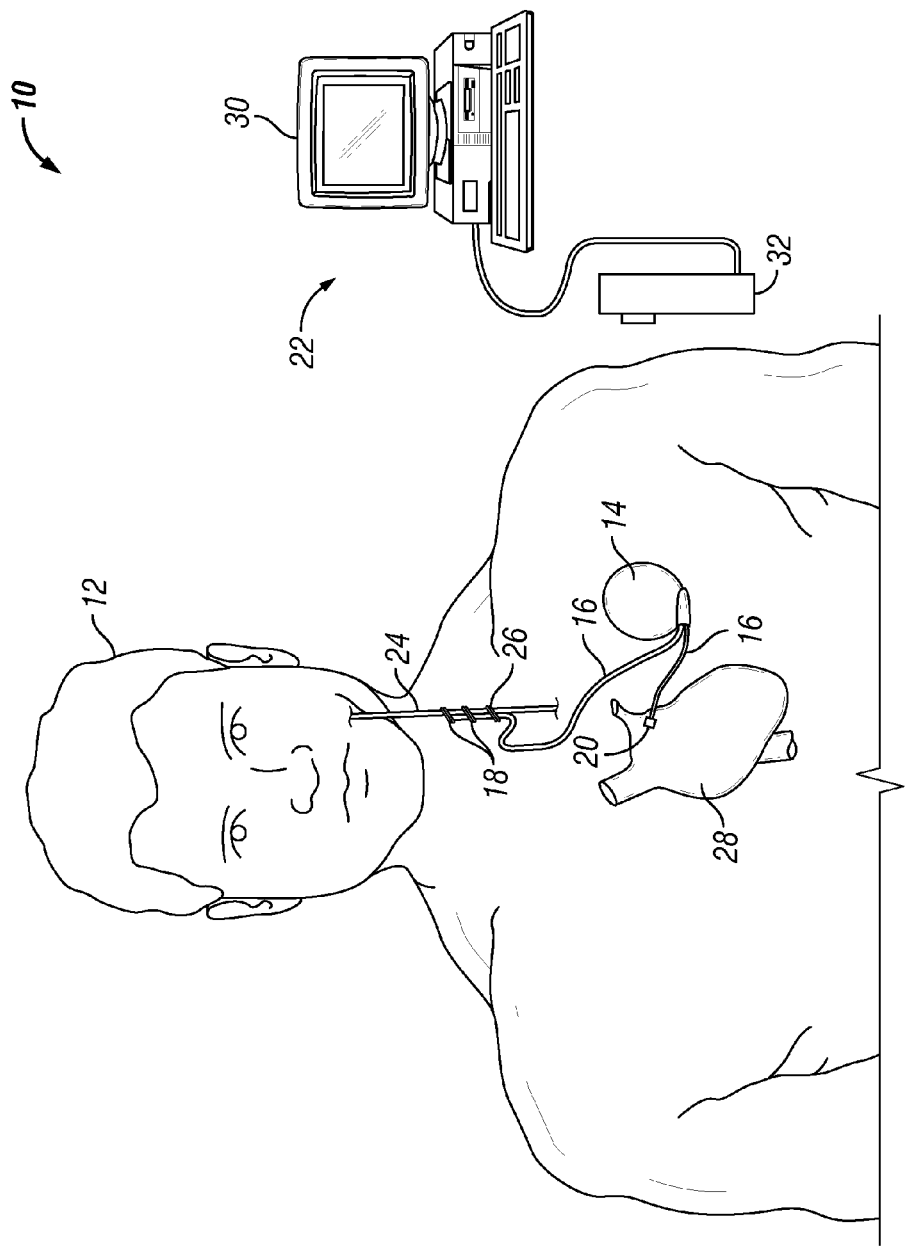
FIGS. 1A and 1B illustrate medical treatment systems, according to certain embodiments.
Figure 1B:
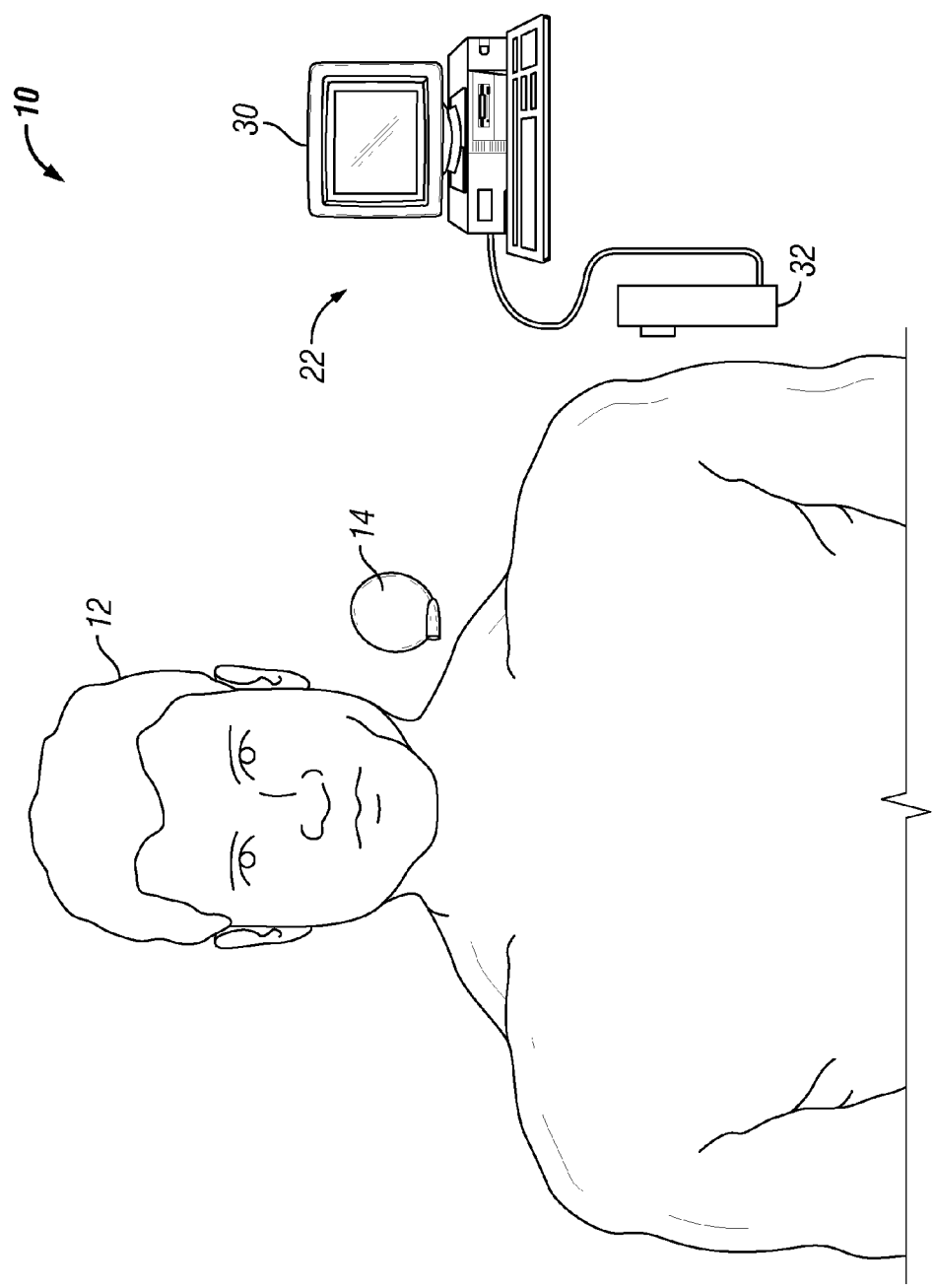

FIGS. 1A and 1B illustrate a medical treatment system 10, according to certain embodiments. System 10 may be configured to detect the occurrence of epileptic seizures, or an elevated risk of a seizure, experienced by a patient 12, and to take one or more responsive actions to the detection. Responsive actions may include, by way of nonlimiting examples: logging the occurrence and/or time of occurrence of the seizure; providing a warning, alarm or alert to the patient, a caregiver or a health care provider; providing a therapy to prevent, abort, and/or reduce the severity and/or duration of the seizure; assessing one or more patient parameters such as awareness or responsiveness during the seizure; assessing the severity of the seizure, identifying the end of the seizure; and assessing the patient's post-ictal impairment or recovery from the seizure. Providing the warning, alarm or alert may include, for example, sending an email or another type of remote alert or notification to the patient, a caregiver, a responder, a physician, or a combination thereof.

Referring to the embodiment of FIG. 1A, system 10 may prevent and/or reduce seizures by providing a therapy in response to the detection event. In one embodiment, the therapy may comprise applying a closed-loop electrical signal to a neural structure of patient 12. System 10 may be configured to transmit the electrical signal in response to changes in a physiological parameter of patient 12 such as, for example, a change in the heart rate of patient 12. Referring to the embodiment of FIG. 1B, system 10 may detect a seizure event and initiate one or more responsive actions such as logging the occurrence and/or time of the seizure event, recording one or more body parameters before, during or after the event, assess the severity of the seizure event, warn or provide alarms to the patient and/or a caregiver, and take other actions to ensure the safety of the patient. In some embodiments, system 10 may be configured to dynamically adjust the seizure detection threshold in a cardiac-based seizure detection algorithm based at least in part on the current activity level of patient 12. Providing a dynamic, heart rate based threshold for seizure detection may result in fewer false positive detections and an enhanced accuracy for detecting actual seizures and not detecting as seizures heart rate changes that are unrelated to seizures.

Referring again to FIG. 1A, a dynamic threshold may increase the likelihood of system 10 transmitting the electrical signal in response to an actual seizure, and of avoiding transmitting the electrical signal in response to exertional or other non-seizure tachycardia or bradycardia. System 10 may comprise a medical device (MD) 14, such as the implantable medical device (IMD) shown in FIG. 1A, one or more leads 16, one or more stimulators 18, one or more sensors 20, and a programming system 22.

MD 14 may represent any of a variety of medical devices. In some embodiments, MD 14 comprises a neurostimulator for stimulating a neural structure in patient 12. MD 14 may be configured to stimulate any suitable neural structure such as, for example, a cranial nerve 24. Examples of cranial nerves 24 include, but are not limited to, the vagus nerve, cranial accessory nerve, olfactory nerve, optic nerve, oculomotor nerve, trochlear nerve, trigeminal nerve, abducens nerve, facial nerve, vestibulocochlear nerve, glossopharyngeal nerve, hypoglossal nerve, and branches of the foregoing. Although MD 14 is described in FIG. 1A below in terms of vagus nerve stimulation (VNS), MD 14 may be applied to the stimulation of other cranial nerves 24 and/or other neural tissue such as, for example, one or more peripheral nerves, brain structures, spinal nerves, and/or other spinal structures of patient 12.

In some embodiments, MD 14 may be coupled to one or more leads 16. Each lead 16 may comprise a conductive wire (e.g., metallic wire) configured to communicate electrical signals between MD 14 and one or more electrodes. In some embodiments, lead 16 has a proximal end that is coupled to MD 14 as well as a distal end that is coupled to a stimulator 18 and/or a sensor 20. One or more anchor tethers 26 may be incorporated in certain embodiments to couple lead 16 to a tissue structure (e.g., cranial nerve 24) in patient 12. In addition one or more fasteners 27 may be any suitable device for attaching lead 16 to a tissue structure by, e.g., sutures. Anchor tether(s) 26 and fastener(s) 27 may be positioned to reduce or prevent the strain associated with patient movement from being transmitted to lead 16 or stimulator 18.

The distal end of lead 16 may be coupled to stimulator 18 and/or sensor 20. Stimulator 18 may comprise any suitable device for delivering an electrical signal from MD 14 to cranial nerve 24. In some embodiments, stimulator 18 comprises one or more electrodes that deliver electrical current to a target tissue such as, for example, cranial nerve 24 of patient 12. Stimulator 18 may be kept in contact with cranial nerve 24 by using one or more anchor tethers 26 and/or fasteners 27.

System 10 may comprise any suitable number of stimulators 18 communicatively coupled to MD 14.

As explained above, the distal end of one or more leads 16 may be coupled to one or more sensors 20. Sensor 20 may comprise any suitable device for sensing a physiological parameter of patient 12. For example, sensor 20 may be attached to cardiovascular tissue 28 in patient 12 (e.g., the heart) to sense the time of beat sequence of the heart of patient 12. "Time of beat sequence" may refer to a series of timestamps associated with a measured fiducial point (e.g., an R wave peak, a P wave peak, a T wave peak, etc.) in the cardiac cycle of the patient. A series of sequential timestamps for a fiducial point, such a the R wave peak, may be used in a medical device processor to derive a variety of cardiac parameters such as heart rate, heart rate variability, etc. Heart rate may be determined on an instantaneous basis from the immediately preceding 2 fiducial points, or as a median or average heart rate for a window, such as a time window (e.g., 5 seconds, 30 seconds, or 300 seconds), or a number-of-beats window (e.g., 3 beats, 5 beats, 30 beats, or 300 beats). In addition, or alternatively, sensor 20 may be attached to tissue in patient 12 to detect blood pressure, blood sugar, blood pH, blood oxygen level, blood CO2 level, body movement, breathing, pupillary dilation, brain electrical activity and/or any suitable physiological parameter of patient 12.

In some embodiments, sensor 20 may comprise one or more electrodes configured to sense electrical activity in the body of patient 12 (e.g., a voltage indicative of cardiac activity or brain wave activity). In addition, or alternatively, sensor 20 may comprise a pressure transducer, an acoustic element, a photonic element (e.g., light emitting or absorbing element), and/or any suitable element configured to provide a sensing signal representative of a physiological body parameter. In some embodiments, sensor 20 may be a heart rate sensor, a body movement sensor (e.g., a triaxial accelerometer and/or a gyroscope), a blood pH sensor, a blood pressure sensor, and/or a blood sugar sensor. Sensor 20 may be kept in contact with the target tissue in patient 12 in some embodiments by one or more fasteners 27. MD 14 may be coupled via leads 16 to any suitable number and combination of sensors 20.

Any of a variety of suitable techniques may be employed to run lead 16 from an implantable device through the body of patient 12 to an attachment point such as cranial nerve 24 or cardiovascular tissue 28 of patient 12. In some embodiments, an electrode or electrode pair may function both as a stimulator 18 and a sensor 20. In certain embodiments, the outer surface of MD 14 itself may be electrically conductive and may function as a sensor 20. See, for example, U.S. Pat. No. 5,928,272.

Referring to the embodiment of FIG. 1B, system 10 may allow notification and/or tracking of detection events. System 10 may detect a seizure event and initiate one or more responsive actions such as logging the occurrence and/or time of the seizure event, recording one or more body parameters before, during or after the event, assess the severity of the seizure event, warn or provide alarms to the patient and/or a caregiver, and take other actions to ensure the safety of the patient. In some embodiments, system 10 may be configured to dynamically adjust the seizure detection threshold in a cardiac-based seizure detection algorithm based at least in part on the current activity level of patient 12. Providing a dynamic, heart rate based threshold for seizure detection may result in fewer false positive detections and an enhanced accuracy for detecting actual seizures and not detecting as seizures heart rate changes that are unrelated to seizures. MD 14 in system 10 of FIG. 1B may comprise an external medical device (IMD), such as an external heart rate monitor, perhaps associated with patient 12 by using a chest harness, an electronic patch configured to detect heart rate, or the like.

System 10 in FIGS. 1A and 1B may comprise a programming system 22 configured to communicate with MD 14. Programming system 22 may be configured to generally monitor the performance of MD 14. In some embodiments, programming system 22 downloads programming information into MD 14, uploads from MD 14 physiological information collected by sensors 20, and/or alters the operation of MD 14 as desired. In some embodiments, programming system 22 may cause MD 14 to perform one or more calibration processes. Programming system 22 may comprise a computer 30 and a wand 32.

Computer 30 may comprise any suitable processing device such as, for example, a personal computer, personal digital assistant (PDA), smart phone, and/or other suitable computing device. Computer 30 may be coupled to wand 32 by a wired and/or wireless connection. Wand 32 may represent any suitable interface device that allows computer 30 to communicate with MD 14. In some embodiments, wand 32 may be integral with computer 30. When placed in proximity to patient 12, wand 32 may wirelessly upload and/or download information to/from MD 14. In some embodiments, wand 32 may recharge the battery of MD 14 when placed in proximity to patient 12. In external embodiments (FIG. 1B) or in implantable embodiments incorporating data transmission in the Medical Implant Communication Service (MICS) band, wand 32 may be omitted and communication between computer 30 and MD 14 may occur without wand 32. Representative techniques for communicating between MD 14 and programming system 22 are disclosed in U.S. Pat. No. 5,304,206 and U.S. Pat. No. 5,235,980, both of which are incorporated herein by reference.

In some embodiments (FIG. 1A), it may be desirable to apply an electrical signal to cranial nerve 24 of patient 12 when patient 12 is about to experience and/or is experiencing a seizure. Such an electrical signal may prevent, interrupt, or reduce the severity of the seizure. It has been observed that a seizure is often preceded and/or accompanied by an increase in the heart rate of patient 12. In operation, MD 14 may monitor the heart rate of patient 12 and, in response to a change in heart rate, MD 14 may apply an electrical signal to cranial nerve 24. In addition, or alternatively, an external device (e.g., computer 30) may monitor the heart rate of patient 12 and, in response to a change in heart rate, may cause MD 14 to apply an electrical signal to cranial nerve 24 of patient 12.

Whether a change in heart rate is indicative of an actual seizure may depend on the activity level of patient 12. When a typical person is engaged in a sedentary activity such as sleeping, minor changes in activity level, such as merely standing up, may cause a significant increase in heart rate. To avoid detecting such non-ictal cardiac changes as a seizure, MD 14 may be configured to dynamically determine a relatively high threshold for identifying a seizure event when patient 12 is engaged in a sedentary activity. Conversely, when the patient is engaged in a strenuous activity such as running, a relatively high amount of additional effort is required to cause even a moderate increase in heart rate. Thus, to increase the accuracy of identifying seizures, MD 14 may be configured to dynamically determine a relatively low threshold for identifying a seizure event when patient 12 is engaged in a strenuous activity. As explained below with respect to FIG. 3A, when patient 12 experiences a heart rate change that is greater than and/or equal to the dynamic threshold, MD 14 may indicate that a seizure event has occurred, and may in response apply an electrical signal to cranial nerve 24 in order to prevent, interrupt, and/or reduce the severity of a seizure.

Figure 2A:
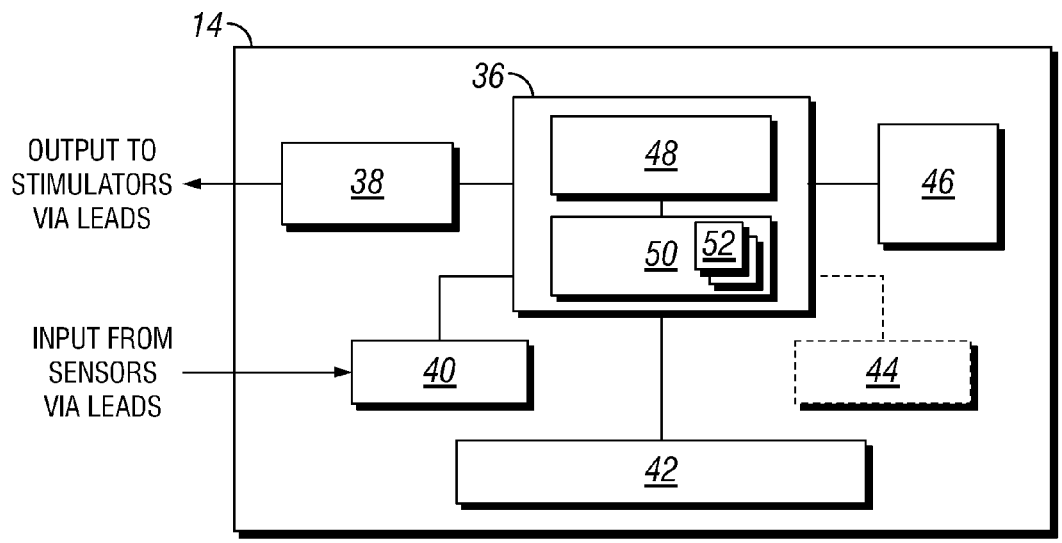
FIGS. 2A and 2B illustrate various components of a medical device, according to certain embodiments.

FIG. 2A illustrates various components of MD 14, according to certain embodiments. MD 14 is generally operable to detect an epileptic seizure event based on the heart rate of a patient 12. MD 14 may comprise a controller 36, a responsive action unit 38, a detection unit 40, a communication unit 42, and a power supply 46. Responsive action unit 38 may comprise hardware and/or firmware to initiate one or more of responsive actions such as alarms, warnings, seizure severity measurement determinations, logging/recording information related to the seizure, or therapies such as electrical stimulation applied via electrodes or other stimulators. An optional electrode selection unit 44 may be provided in some embodiments for applying an electrical signal to a cranial nerve 24 of the patient. In some embodiments, one or more of the foregoing components may be implanted, while in other embodiments portions or all of the components may be external.

Controller 36 in MD 14 is generally operable to control various aspects of the operation of MD 14. MD 14 may receive body data signals from sensors into detection unit 40 for processing under the control of controller 36. Detection unit 40 may detect a seizure event associated with changes in the patient's heart rate by an algorithm comparing one or more heart rate parameters to a dynamic threshold. In some embodiments, controller 36 may cause responsive action unit 38 to initiate one or more responsive actions such as generating a warning or alarm to a patient or caregiver; determining and recording or logging a time of the seizure, a duration of the seizure, one or more seizure severity measures; and determination and recording other seizure metrics or autonomic/neurologic events associated with the seizure event detected. In some embodiments, such as shown in FIG. 2A, responsive action unit 38 may initiate delivery of an electrical signal to target tissues in order to treat a detected seizure event. Controller 36 may cause the electrical signal to be generated and delivered based at least in part on internal calculations and programming. In addition, or alternatively, controller 36 may receive and respond to manual instructions from a patient or caregiver. In some embodiments, controller 36 comprises a processor 48 and a memory 50.

Processor 48 may comprise one or more microcontrollers, microprocessors, and/or other suitable hardware capable of executing various software components. Processor 48 may be communicatively coupled to memory 50.

Memory 50 may comprise one or more tangible, computer-readable media that are generally operable to store any suitable type and/or combination of data such as, for example, internal data instructions, external data instructions, software codes, status data, and/or diagnostic data. Memory 50 may comprise random access memory (RAM), dynamic random access memory (DRAM), electrically erasable programmable read-only memory (EEPROM), flash memory, and/or any suitable type and/or combination of memory devices. In some embodiments, memory 50 may store one or more patient profiles 52.

Patient profile 52 may comprise historical and/or current data associated with the treatment of patient 12, and/or historical data for other patient groups or cohorts. In some embodiments, profile 52 comprises historical and/or current data reflecting the heart rate of patient 12 and/or other patients at various times. Profile 52 may comprise one or more instructions (e.g., charts, algorithms, graphs, and/or look-up tables) that specify when MD 14 should detect a seizure event and initiate a responsive action. Memory 50 may store any suitable number of profiles 52.

In some embodiments, MD 14 comprises a responsive action unit 38 that is communicatively coupled to controller 36. Responsive action unit 38 may initiate any of a variety of responsive actions. In one embodiment, the responsive action unit may log one or more timestamps, set one or more flags, and initiate a real-time storage sequence of body data of the patient. The responsive action unit may comprise one or more sub-modules to analyze body data before and/or after the detection event to determine and store one or more seizure metrics associated with the seizure event. In one embodiment, the responsive action unit may comprise a seizure severity sub-module to determine an indication of seizure severity, which may include one or more parameters such as the maximum heart rate of the patient following the seizure detection, the time interval from detection of the seizure to maximum heart rate, the time interval from the seizure detection until the patient's heart rate returns to its pre-ictal rate. Other seizure metrics, such as the inter-seizure interval between the detected seizure event and the immediately preceding seizure, may also be determined and stored for later reporting. Responsive action unit may comprise suitable circuitry for the logging, warning and analyzing body data including, without limitation, memory modules or sub-modules, control logic and/or programs, look-up tables, etc. The actions performed by the responsive action unit 38, or its sub-modules, may be executed under the control of controller 36, and may be coupled to other components of MD 14 such as detection unit 40, discussed hereinafter.

Responsive action unit 38 may further initiate a responsive therapy such as an electrical stimulation therapy to a cranial nerve, and may comprise one or more sub-modules to provide the therapy. In one embodiment, a therapy sub-module may generate and/or transmit an electrical signal to one or more stimulators 18 via leads 16. The therapy sub-module of responsive action unit 38 may deliver the electrical signal to leads 16 based upon instructions from controller 36. A therapy sub-module of responsive action unit 38 may comprise any suitable circuitry such as, for example, stimulation signal generators, impedance controllers (e.g., circuitry to control the impedance "seen" by leads 16), and/or other suitable circuitry that receives instructions relating to the delivery of the electrical signal to tissue. In some embodiments, responsive action unit 38 may be configured to deliver a controlled current electrical signal over leads 16.

In addition, or alternatively, MD 14 may comprise a detection unit 40 that is communicatively coupled to controller 36. Detection unit 40 is generally operable to detect and/or determine one or more physiological parameters of patient 12. For example, detection unit 40 may detect physiological parameters relevant to a medical condition such as, for example, epilepsy or depression. In some embodiments, detection unit 40 may detect the cardiac time of beat sequence of patient 12. For example, sensors 20 in proximity to the heart of patient 12 may transmit to detection unit 40 one or more signals associated with the cardiac cycle of patient 12, such as a sequence of R-wave detections from which heart rate and other cardiac parameters (e.g., heart rate variability calculations) may be determined. An "R-wave" refers to the peak of the upward deflection of the QRS complex in an electrocardiogram. Detection unit 40 may comprise any suitable hardware, software, and/or firmware configured to detect and/or interpret signals associated with physiological parameters of patient 12. Detection unit 40 may also comprise software for detection of an epileptic seizure event, which may comprise an actual seizure and/or an elevated risk of an imminent seizure. In some embodiments, in response to information collected by detection unit 40, MD 14 may cause responsive action unit 38 to initiate a responsive action such as logging, analyzing or providing a therapy to patient 12. In addition, or alternatively, detection unit 40 may detect and monitor quality of life indication(s), seizure frequency parameter(s), seizure characteristic parameter(s), side effect parameter(s), brain-activity parameter(s), depression score parameters, and/or medication dosage parameter(s) associated with patient 12.

Figure 2B:
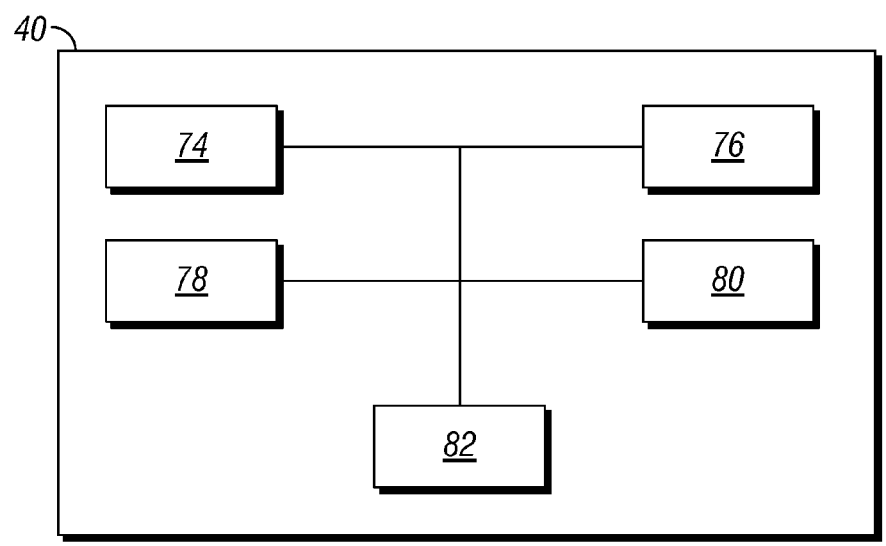

FIG. 2B shows further detail of detection unit 40 according to one embodiment, though other embodiments are possible where at least some of the modules shown are not in detection unit 40 and/or additional modules not shown are included. Detection unit 40 in FIG. 2B includes a heart rate determination module 74 configured to identify from the time of beat sequence a change in heart rate of the patient from a first heart rate to a second heart rate. Detection unit 40 also includes a parameter determination module 76 configured to determine at least one of 1) a ratio of the second heart rate to the first heart rate and 2) a difference between the second heart rate and the first heart rate. Detection unit 40 further includes a dynamic threshold determination module 78 configured to determine at least one of 1) a dynamic ratio threshold for the ratio and 2) a dynamic difference threshold for the difference, wherein the at least one threshold is based upon the first heart rate. Detection unit 40 still further includes a comparison module 80 configured to compare at least one of 1) the ratio to the dynamic ratio threshold and 2) the difference to the dynamic difference threshold. Detection unit 40 additionally includes a neurologic event detection module 82 configured to detect a neurologic event when at least one of 1) the ratio exceeds the dynamic ratio threshold and 2) the difference exceeds the dynamic difference threshold.

MD 14 may comprise a communication unit 42 communicatively coupled to controller 36. Communication unit 42 may comprise any suitable hardware, software, and/or firmware configured to facilitate communications between MD 14 and a programming system, (e.g., programming system 22 shown in FIG. 1). In a particular embodiment, communication unit 42 may permit the transmission and reception of electronic signals to and from processor 48 and/or wand 32. As explained above, an operator of system 10 may use processing system to download information from MD 14, upload information to MD 14, configure treatment parameters stored in MD 14, and/or modify instructions in MD 14 that govern the responsive action unit 38.

In some embodiments, MD 14 may comprise an electrode selection unit 44 that is communicatively coupled to controller 36. Electrode selection unit 44 may direct an electrical signal to one or more of a plurality of stimulators 18 that are operationally coupled to various portions of cranial nerve 24 of patient 12. For example, in embodiments where cranial nerve 24 is the vagus nerve, electrode selection unit 44 may direct an electrical signal to the left vagus main trunk, the right vagus main trunk, both the left and right vagus main trunks, and/or a branch of the left and/or right vagus nerves. In addition, or alternatively, electrode selection unit 44 may "steer" the electrical pulse to particular nerve axons within the main vagus nerve trunk by selecting particular electrodes from among a plurality of stimulators 18 coupled to portions of the vagus nerve. In this way, MD 14 may target a predetermined portion of the vagus nerve. Responsive to one or more parameters determined by detection unit 40, electrode selection unit 44 may provide an electrical signal capable of generating afferent action potentials, efferent action potentials, blocking afferent potentials, and/or a combination of the foregoing effects. Electrode selection unit 44 may comprise any suitable hardware, software, and/or firmware configured to perform the foregoing functions and/or operations.

Controller 36 in MD 14 may be communicatively coupled to a power supply 46. Power supply 46 may comprise any suitable components (e.g., battery, voltage regulators, capacitors, etc.) to provide power for the operation of MD 14. Power supply 46 may provide power for the generation and/or delivery of an electrical signal to cranial nerve 24 via responsive action unit 38. Power supply 46 may comprise a power source that, in some embodiments, is rechargeable. In other embodiments, power supply 46 may comprise a non-rechargeable power source. In some embodiments, power supply 46 comprises a lithium/thionyl chloride cell and/or a lithium/carbon monofluoride (LiCFx) cell. It should be understood, however, that other suitable battery types may be used.

Figure 3A:
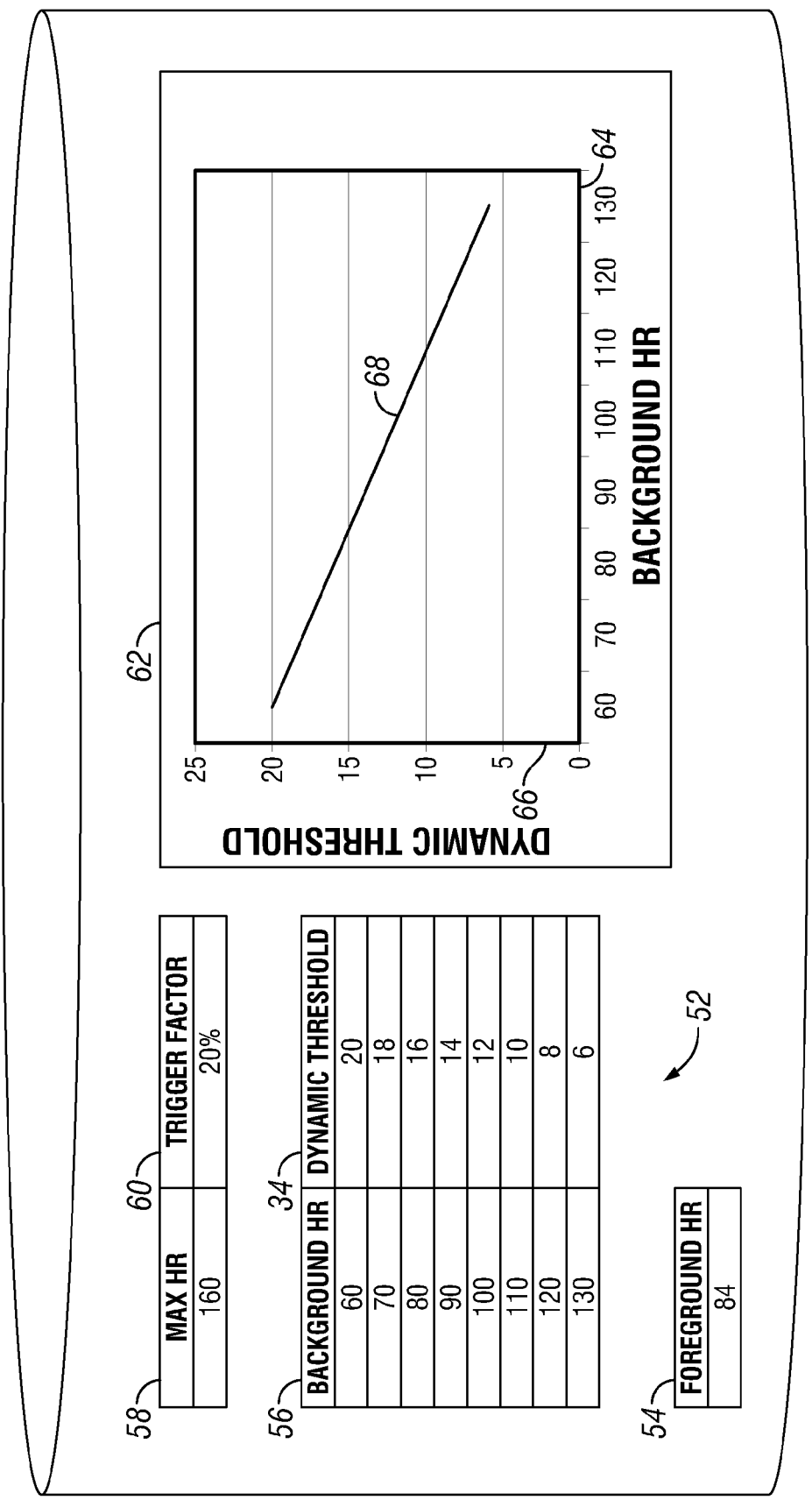
FIGS. 3A and 3B illustrate patient profiles stored in memory in an implantable medical device, according to certain embodiments.

FIG. 3A illustrates an illustrative and non-limiting patient profile 52 according to one embodiment. Profile 52 may be stored in memory 50 in MD 14. According to certain embodiments. MD 14 may use information stored in profile 52 to determine a dynamic threshold for detecting an onset or imminent onset of an epileptic seizure. In some embodiments, MD 14 determines (e.g., in detection unit 40, FIGS. 2A and 2B) a foreground heart rate 54 of patient 12 in a short-term window, and a background heart rate 56 of patient 12 in a long-term window. The windows may be time or number-of-beats windows, and at least a portion of the long-term window occurs prior to the short-term window. At least the short-term window may end in a present time. In addition, in some embodiments, profile 52 may also store a maximum heart rate 58 of patient 12, one or more dynamic thresholds 34, and/or one or more trigger factors 60.

The foreground heart rate 54 of patient 12 generally refers to the heart rate of patient 12 in a short-term window. In some embodiments, this may comprise an instantaneous heart rate determined from the immediately preceding two R-wave detections, e.g., HRst=60/(RRI), where HRst is short-term heart rate and RRI is the R-R interval determined from the two most recent R-wave detections. In other embodiments, a short-term window (e.g., 5 seconds) may be used and a statistical measure of central tendency (e.g., median or mean) for the short-term window may be used as the short-term heart rate. Use of a short-term window instead of an instantaneous heart rate as the foreground heart rate measure may smooth the heart rate and improve accuracy by removing rapid fluctuations from providing erroneous detection events.

As explained above, MD 14 may monitor and store in memory 50 the time of beat sequence of each heartbeat of patient 12. Using this information, MD 14 may determine the foreground heart rate 54 of patient 12 based at least in part on the timing of the most recent heartbeats of patient 12. For example, MD 14 may determine the foreground heart rate 54 based at least in part on the frequency of the most recent five heartbeats, the most recent ten heartbeats, the beats occurring in the most recent five-second or ten-second moving window, and/or other suitable short-term window. MD 14 may continuously update the foreground heart rate 54.

In addition to the foreground heart rate 54, MD 14 may determine and store a background heart rate 56 of patient 12 in profile 52. The background heart rate 56 may represent a statistical measure of central tendency (e.g., median, average) of heart rate for patient 12 over a longer period of time than the foreground heart rate, and at least a portion of the background heart rate window occurs prior to the foreground heart rate window. In one embodiment, the background window is a window immediately preceding the foreground window. In one exemplary embodiment, the background heart rate 56 of patient 12 at any given time represents the average heart rate of patient 12 over the preceding two minutes. In other embodiments, the background heart rate 56 represents the median heart rate of the immediately preceding 500 R-R intervals. Any suitable period of time may be used for calculating the background heart rate 56, so long as the background time period is longer than the foreground time period and includes at least a portion of time preceding the foreground window. The background window may occur entirely prior to the foreground window in some embodiments, although in other embodiments the background window may overlap at least a portion of the foreground window.

In some embodiments, the background heart rate 56 represents the average heart rate of patient 12 during a period comprising a programmable number of heartbeats or a programmable time window. For example, the background heart rate 56 may represent the median heart rate during the most recent three hundred heartbeats (i.e., R-R intervals). In some embodiments, weighting techniques such as exponential forgetting may be used to determine the background heart rate for the background window. As another example, the background heart rate 56 may represent the average (mean) heart rate occurring in the most recent five hundred seconds, or in the most recent 500 seconds preceding the foreground window. In some embodiments, the background heart rate 56 may be determined based at least in part on a time interval that varies as the heart rate of patient 12 changes.

In some embodiments, profile 52 comprises the maximum heart rate 58 of patient 12. The maximum heart rate 58 may represent an approximation of the maximum rate at which the heart of patient 12 is able to beat in non-pathological conditions. For example, the maximum heart rate 58 may represent the heart rate of patient 12 when he/she is exerting maximum physical effort. The maximum heart rate 58 may be determined by a caregiver of patient 12 prior to and/or after MD 14 is implanted in patient 12. From time to time, and as the physical conditioning of patient 12 changes, the doctor of patient 12 may use programming system 22 to update the maximum heart rate 58 stored in profile 52. If patient-specific data is not available, known maximum heart rate formulas (e.g., HRmax=220−patient age in years), may be used.

In some embodiments, profile 52 may comprise one or more trigger factors 60. The trigger factor 60 may represent a percentage that MD 14 uses to determine when a seizure event has been detected. The trigger factor 60 may be a percentage of a difference between a maximum heart rate of the patient and the first heart rate. The percentage may be between fifteen percent and thirty-five percent. Trigger factor 60 may be used in the calculation of dynamic threshold 34 as described below in the discussion of FIGS. 3A and 3B. In one embodiment, trigger factor 60 may be programmed by a healthcare provider in order to make MD 14 more or less responsive to changes in the foreground heart rate 54 of patient 12 in detecting seizures. That is, as trigger factor 60 increases, it may cause dynamic threshold 34 to be less responsive to changes in foreground heart rate 54 even though an equation for calculating dynamic threshold remains the same.

In some embodiments, MD 14 uses the trigger factor 60, the maximum heart rate 58, and the background heart rate 56 of patient 12 to determine a dynamic threshold 34 for seizure detection. MD 14 may store one or more dynamic thresholds 34 in profile 52. Dynamic threshold 34 is used to adjust the sensitivity of a seizure detection algorithm to detect seizure events based on changes in the patient's level of activity, as reflected in the background heart rate. For example, when patient 12 is sedentary (e.g., sitting or sleeping), the background heart rate 56 of patient 12 is generally low. At such times, because MD 14 determines the dynamic threshold 34 based at least in part on the background heart rate 56, MD 14 may require a relatively large change in the foreground heart rate 54 before MD 14 will detect a seizure event. Conversely, when patient 12 is active (e.g., walking, running or swimming), the background heart rate 56 of patient 12 is relatively high. Accordingly, at such times, MD 14 may require only a small or moderate change in the foreground heart rate 54 before detecting a seizure event.

As illustrated in FIG. 3A, profile 52 may comprise a plurality of dynamic thresholds 34 for different background heart rates 56. Alternatively, mathematical equation relating background heart rate and dynamic threshold may be used by IMD 14, such as in detection unit 40, to periodically or continuously determine a dynamic threshold in real-time or near real-time for use in a cardiac-based seizure detection algorithm. An example of such an algorithm is provided in U.S. patent application Ser. No. 12/770,562, where is hereby incorporated herein in its entirety. The use of dynamic thresholds as described herein may be used to reduce the false positive and/or negative detection rates of such cardiac-based algorithms.

It has been observed that a seizure is often preceded or accompanied by a change (usually but not always an increase) in the foreground heart rate 54 of patient 12. Thus, by monitoring the heart rate of patient 12, MD 14 may be configured to detect a seizure in response to a significant change (typically an increase) in the foreground heart rate 54.

Whether an increase in the foreground heart rate 54 constitutes a change that is indicative of a seizure may depend on the current activity level of patient 12. When a typical person is engaged in a sedentary activity such as sleeping, merely standing up may cause a significant increase in heart rate. To avoid detecting a seizure event based on such non-seizure transient changes in heart rate, MD 14 may be configured to calculate a relatively high dynamic threshold 34 when patient 12 is engaged in a sedentary activity (typically associated with a relatively low background heart rate 56).

Conversely, when a typical person is engaged in a strenuous activity such as running, a relatively high amount of additional effort is required to cause even a moderate increase in heart rate. Thus, to increase the seizure detection accuracy of MD 14 at such times, MD 14 may be configured to establish a relatively low dynamic threshold 34 when patient 12 is engaged in a strenuous activity (typically associated with a relatively high background heart rate 56).

An example from FIG. 3A illustrates certain embodiments of the dynamic threshold 34 and how it may be determined. In the present example, MD 14 monitors a patient 12 with a maximum heart rate 58 of one hundred and sixty beats per minute (160 bpm). MD 14 may store the maximum heart rate 58 for patient 12 in profile 52. In certain embodiments, a trigger factor 60 may be used to determine dynamic threshold values associated with particular background heart rates 56. In the example of FIG. 3A, a trigger factor of twenty percent is shown.

MD 14 may calculate a dynamic threshold 34 (DT) by multiplying the trigger factor 60 (TF) by the difference between maximum heart rate 58 (HRmax) and background heart rate 56 (HRbg) as shown in equation 1.

$$DT=TF*(HRmax-HRbg) \qquad (1)$$

For a background heart rate 56 of sixty beats per minute (60 bpm), the difference between the background heart rate 56 and the maximum heart rate 58 of patient 12 is one hundred beats per minute (100 bpm). Multiplying this difference by the trigger factor yields a dynamic threshold 34 for a background heart rate of 60 bpm of twenty beats per minute (i.e., DT=0.2*(160 bpm−60 bpm)=20 bpm). Thus, if the patient 12 has a background heart rate at a given time of sixty beats per minute, and if the foreground heart rate suddenly has increased by twenty beats per minute or more, then MD 14 will detect a seizure event in one embodiment.

In the present example, MD 14 may determine a dynamic threshold 34 for different background heart rates 56, and may do so in some embodiments on a real-time basis. As illustrated in the table of dynamic threshold values shown in FIG. 3A, as the background heart rate 56 increases, the respective dynamic threshold 34 decreases. For example, when patient 12 is exercising, the background heart rate 56 of patient 12 may be one hundred and thirty beats per minute, in which case the difference between the maximum heart rate 58 of patient 12 (160 bpm) and the background heart rate 56 of patient 12 (130 bpm) is thirty beats per minute (30 bpm). By multiplying this difference between the background and the maximum heart rates by the trigger factor 60, MD 14 may determine that the particular dynamic threshold 34 for patient 12 in this situation is six beats per minute (i.e., DT=0.2*(160 bpm–130 bpm)=6 bpm). Thus, if the background heart rate 56 of patient 12 at a given time is one hundred and thirty beats per minute if the foreground HR exceeds the background HR by six beats per minute or more, then detection unit 40 will detect a seizure event, and responsive unit 38 will initiate one or more responsive actions.

By configuring the dynamic threshold 34 for detecting a seizure event in response to the current activity level of patient 12 (as embodied in the background HR), MD 14 may increase the accuracy of detecting a seizure (i.e., a true positive detection) and of avoiding false positive detections of non-ictal HR changes.

Figure 3B:
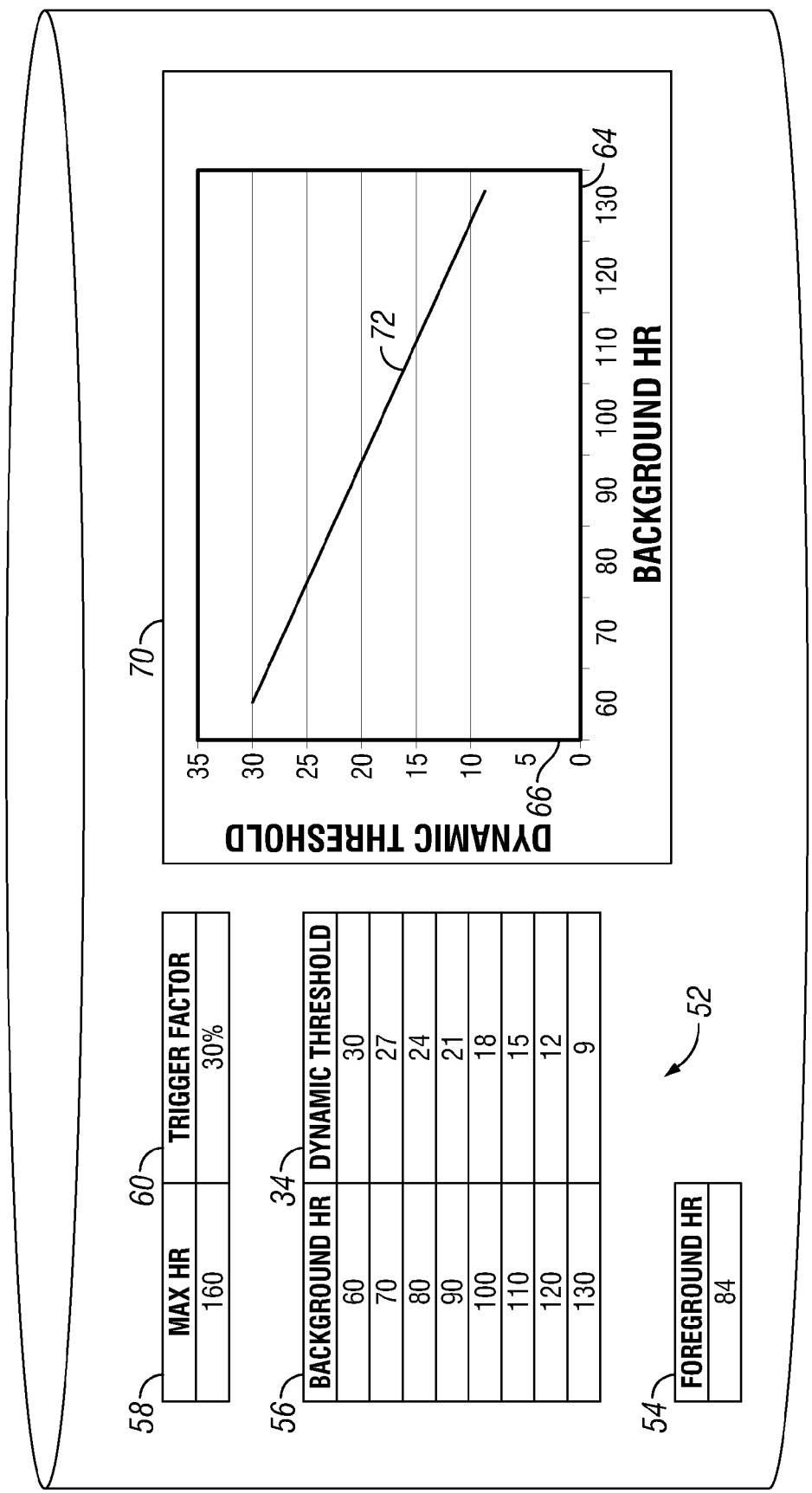

As illustrated, graph 62 in profile 52 shows that, as the background heart rate 56 of patient 12 increases, the dynamic threshold 34 may decrease. In graph 62, the x-axis 64 may represent the background heart rate 56 of patient 12, and the y-axis 66 may illustrate the dynamic threshold 34 for detecting a seizure event based on the foreground and background heart rates. Line 68 may represent the relationship between the background heart rate 56 and the dynamic threshold 34 for a trigger factor 60 of twenty percent. Although a linear relationship is depicted in FIG. 3A, nonlinear relationships such as second or higher order polynomials (or nonlinear graphs/tables) may also be used to determine dynamic thresholds from background heart rate. Polynomials (or nonlinear graphs/tables) may also be derived that are unique for each patient As explained above, prior to and/or after implanting MD 14 in patient 12, a healthcare provider may programmably determine the value of trigger factor 60 in profile 52 of patient 12. FIG. 3B illustrates a patient profile 52 having a trigger factor 60 of thirty percent (30%), in contrast to the trigger factor of twenty percent (20%) used in FIG. 3A. In FIG. 3B, MD 14 monitors heart rate in a patient 12 with a maximum heart rate 58 of one hundred and sixty beats per minute (160 bpm). Using a trigger factor 60 of thirty percent (30%), MD 14 may determine dynamic thresholds 34 based at least in part on background heart rates 56. MD 14 is configured to calculate a dynamic threshold 34 by multiplying the trigger factor 60 by the difference between the background heart rate 56 and the maximum heart rate 58 according to equation 1.

For instance, for a background heart rate 56 of sixty beats per minute (60 bpm), MD 14 determines that the difference between the background heart rate 56 and the maximum heart rate 58 of patient 12 is one hundred beats per minute (100 bpm). By multiplying this difference by the trigger factor 60, MD 14 determines that the particular dynamic threshold 34 for patient 12 in this situation is thirty beats per minute (i.e., DT=0.3*(100 bpm)=30 bpm). Thus, if the background heart rate 56 of patient 12 at a given time is sixty beats per minute (60 bpm) and if the foreground heart rate of patient 12 exceeds ninety beats per minute (90 bpm) or more, then detection unit 40 will detect a seizure event, and response unit 38 will initiate one or more responses as previously discussed.

Graph 70 in profile 52 shows that, as the background heart rate 56 of patient 12 increases, the dynamic threshold 34 may decrease. Line 72 may represent the relationship between the background heart rate 56 and the dynamic threshold 34 for a trigger factor 60 of thirty percent. As previously noted, although a linear relationship between background HR and dynamic threshold is illustrated in FIG. 3B, nonlinear mathematical functions and/or graphs may also express the background HR/dynamic threshold relationship.

Although the foregoing examples illustrate constant trigger factors 60, it should be understood that MD 14 may be configured to use non-constant trigger factors 60 to determine appropriate dynamic thresholds 34. Similarly, although the foregoing examples illustrate a particular maximum heart rate 58 of patient 12, it should be understood that MD 14 may be configured with any maximum heart rate 58 depending at least in part on the physical conditioning and health of particular patients 12. In the foregoing examples, MD 14 determined dynamic thresholds 34 based at least in part on trigger factors 60 and maximum heart rates 58. In other embodiments, MD 14 may be configured to determine appropriate dynamic thresholds 34 by referring to one or more look-up tables that are stored in memory 50 and that are indexed based at least in part on the maximum heart rate 58, the resting heart rate, the foreground heart rate 54, and/or the background heart rate 56 of patient 12.

More generally, in some embodiments, no trigger factor is used, and the dynamic threshold may be determined directly from a mathematical function or graph of the background HR/dynamic threshold relationship. It will be appreciated that, while the dynamic threshold may be a nonlinear function of background heart rate, the detection of a seizure may be determined from a background heart rate, a foreground heart rate, and a dynamic threshold that is a function of the background heart rate. If an equation, graph, or look-up table describing the relationship between the background heart rate and a dynamic threshold (which may be a difference threshold as illustrated in FIGS. 3A and 3B or a ratio threshold of the foreground and background rates) is established—similar to linear graphs 62 and 70 in FIGS. 3A and 3B—there is no need for a trigger factor, and the seizure detection algorithm may simply dynamically adjust one or both of a ratio and a difference threshold according to the value of the background heart rate and the relationship set forth between the background HR and the equation, graph, or table.

Accordingly, for the embodiments herein, the phrase "at least one of a ratio of the second heart rate to the first heart rate and a difference between the second heart rate and the first heart rate," or the like, refers to a ratio of the second heart rate to the first heart rate, a difference between the second heart rate and the first heart rate, or both. Likewise, the phrase "at least one of a dynamic ratio threshold and a dynamic difference threshold," or the like, refers to a dynamic ratio threshold, a dynamic difference threshold, or both. Also, the phrase "at least one of a maximum heart rate and a resting heart rate," or the like, refers to a maximum heart rate, a resting heart rate, or both. Further, the phrase "at least one of a patient, a caregiver, a responder, and a physician," or the like, refers to a patient, a caregiver, a responder, a physician, or a combination thereof.

In still other embodiments, additional information, such as an accelerometer, may be used to confirm an exercise level of the patient, and the need for a dynamic adjustment to a seizure detection threshold. Although linear functions of background HR vs. dynamic threshold are shown, more complex relationships may also be determined either empirically or based on nonlinear mathematical functions.

In some embodiments, MD 14 may be configured to determine the dynamic threshold 34 based at least in part on the background heart rate 56 and the resting heart rate of patient 12. For example, MD 14 may be configured to determine the dynamic threshold 34 based at least in part on a quotient determined by dividing the background heart rate 56 by the difference between the background heart rate 56 (HRbg) and the resting heart rate (HRr) of patient 12 according to equation 2.

$$DT=HRbg/(HRbg-HRr) \quad (2)$$

As another example, MD 14 may be configured to determine the dynamic threshold 34 based at least in part on a quotient determined by dividing the resting heart rate by a difference between the background heart rate 56 and the resting heart rate according to equation 3.

$$DT=HRr/(HRbg-HRr) \quad (3)$$

Thus, various techniques may be used to determine a dynamic threshold 34 that decreases as the background heart rate 56 of patient 12 increases.

Figure 4:
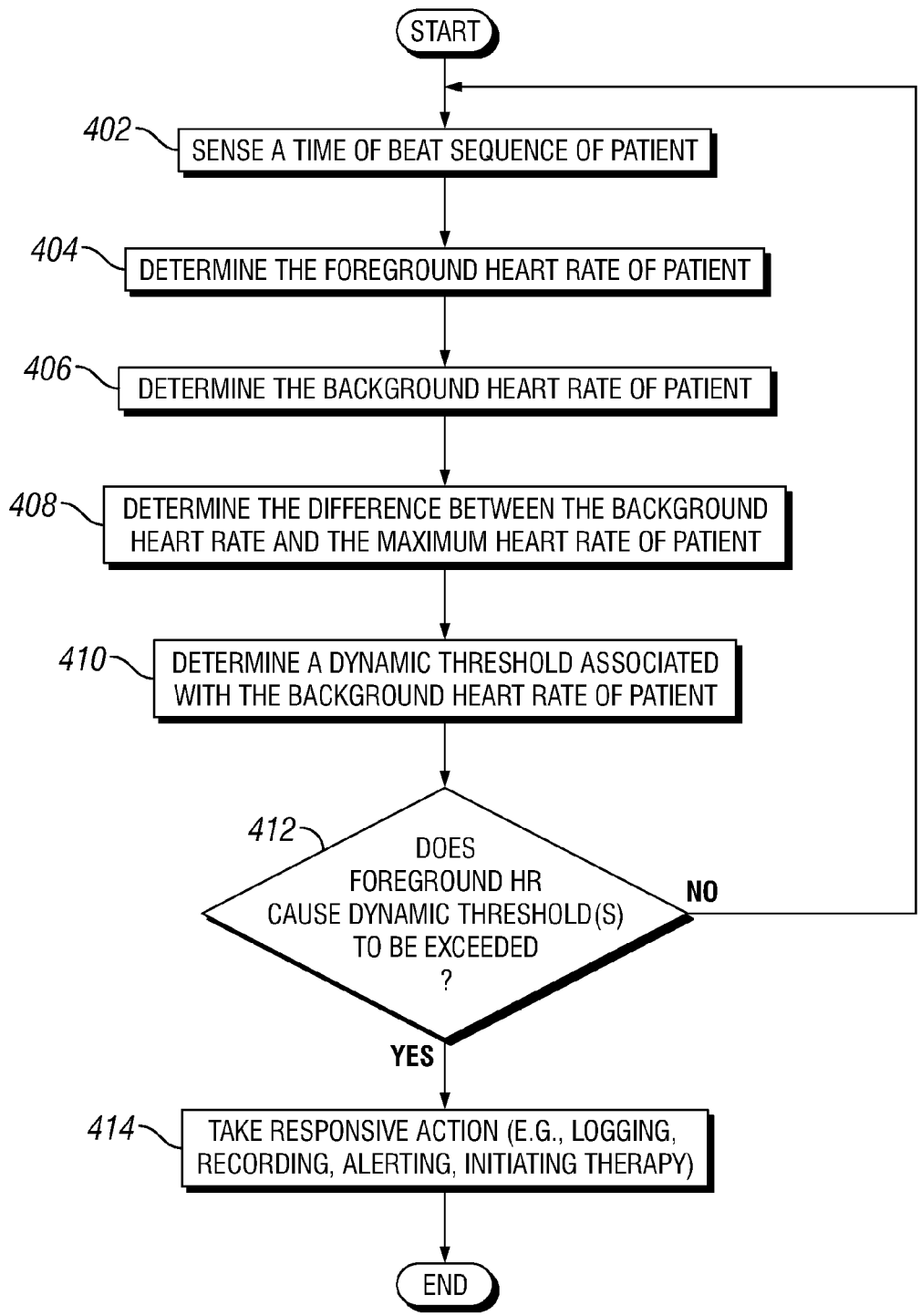
FIG. 4 illustrates a flowchart for a method of delivering an electrical signal to a cranial nerve of a patient, according to certain embodiments.

FIG. 4 illustrates a flowchart for a method of delivering electrical pulses to cranial nerve 24 of patient 12, according to certain embodiments. The method begins at step 402 by sensing a time of beat sequence of patient 12. MD 14 may sense the time of beat sequence via sensors 20 that are implanted in patient 12 near his or her heart. Controller 36 in MD 14 may store historical and/or current information associated with the time of beat sequence in patient profile 52 in memory 50.

The method continues at step 404 by determining a foreground heart rate of a patient 12. MD 14 may determine the foreground heart rate 54 of patient 12 based at least in part on the timing of the most recent heartbeats of patient 12 in a short-term window (e.g., the most recent five heartbeats, the beats in a five second moving window, etc.). The foreground rate may be a statistical measure of central tendency of the beats in the short-term window. MD 14 may continuously monitor the foreground heart rate 54 of patient 12.

The method continues at step 406 by determining a background heart rate 56 of patient 12. In some embodiments, the background heart rate 56 represents a statistical measure of central tendency in a long-term window. In some embodiments, at least a portion of the long-term window is prior to the time period of the short-term window. In some embodiments, the long-term window is programmable (e.g., the preceding two minutes, the preceding 200 heart beats, etc.). In other embodiments, the background heart rate 56 represents the average heart rate of patient 12 over a configurable number of heartbeats (e.g., the most recent three-hundred heartbeats, the most recent five-hundred heartbeats, etc.). In some embodiments, the period of time used to determine the background heart rate 56 is longer than the period of time used to determine the foreground heart rate 54.

The method continues at step 408 by determining the difference between the background heart rate 56 and the maximum heart rate 58 of patient 12. The maximum heart rate 58 may represent an approximation of the maximum rate at which the heart of patient 12 is able to beat. For example, the maximum heart rate 58 may represent the heart rate of patient 12 when he/she is exerting maximum physical effort. In some embodiments, the maximum heart rate may simply be determined by a formula, without regard to the patient's specific condition. In some embodiments, the maximum heart rate may be programmably determined by, e.g., a healthcare provider. In some embodiments, such as where a mathematical and/or graphical relationship between dynamic threshold and heart rate is known, step 408 may be omitted.

The method continues at step 410 by determining a dynamic threshold 34 that is a function of the background heart rate 56 of patient 12. In some embodiments, the dynamic threshold 34 may also be determined based at least in part on a trigger factor 60. In one embodiment, the dynamic threshold is determined as a function of a trigger factor 60 and the difference between the background heart rate 56 and at least one of the maximum heart rate (HRmax) 58 and a resting heart rate (HRr) of patient 12. Because MD 14 may determine the dynamic threshold 34 based in part on the background heart rate 56, the sensitivity of MD 14 to identifying a seizure event based on the foreground heart rate 54 and the background rate may change as patient 12 changes his/her level of activity.

The method continues at step 412 by determining whether the foreground rate 54 exceeds the background heart rate 56 by more than the dynamic difference threshold (or the foreground/background rate ratio exceeds the dynamic ratio threshold) 34. If MD 14 determines at step 412 that foreground heart rate 54 does not exceed the background heart rate by more than the dynamic difference threshold (and/or the foreground/background ratio does not exceed the dynamic ratio threshold), the method returns to step 402. However, if MD 14 determines at step 412 that the foreground heart rate 54 exceeds the background heart rate 56 by more than the dynamic threshold 34, then a seizure event has been detected and the method proceeds to step 414.

At step 414, MD 14 initiates one or more responsive actions such as logging, recording, determining one or more seizure metrics, and initiating a therapy such as an electrical signal therapy applied to a cranial nerve 24 of patient 12 in order to prevent and/or reduce the severity of a seizure of patient 12. The method may then conclude. Alternatively, the method may return to step 402 in order to continue monitoring the foreground heart rate 54 of patient 12.

In an embodiment, an article of manufacture may comprise a computer-readable storage medium having programming configured to cause processing circuitry to perform processing including the methods described herein. The processing circuitry may be part of a medical device and may be arranged to process data, control data access and storage, issue commands, and control other desired operations. Processing circuitry may comprise circuitry configured to implement desired programming provided by appropriate media. For example, the processing circuitry may be implemented as one or more of a processor and/or other structure configured to execute executable instructions including, for example, software and/or firmware instructions, and/or hardware circuitry. Processing circuitry may include hardware logic, PGA, FPGA, ASIC, state machines, and/or other structures alone or in combination with a processor. These examples of processing circuitry are for illustration and other configurations are possible.

The storage medium may be included within a medical device or may be present as a part of a medical device system, and is configured to store programming such as executable code or instructions (e.g., software and/or firmware), electronic data, databases, or other digital information and may include processor-usable media. Processor-usable media may be embodied in any computer program product(s) or article of manufacture(s) that can contain, store, or maintain programming, data and/or digital information for use by or in connection with an instruction execution system including the processing circuitry. For example, suitable processor-usable media may include physical media such as electronic, magnetic, optical, electromagnetic, infrared or semiconductor media. Some more specific embodiments of processor-usable media include, but are not limited to, a portable magnetic computer diskette (such as a floppy diskette, zip disk, hard drive), random access memory, read only memory, flash memory, cache memory, and/or other configurations capable of storing programming, data, or other digital information.

The present disclosure encompasses all changes, substitutions, variations, alterations and modifications to the example embodiments described herein that a person having ordinary skill in the art would comprehend. Similarly, where appropriate, the appended claims encompass all changes, substitutions, variations, alterations, and modifications to the example embodiments described herein that a person having ordinary skill in the art would comprehend.

What is claimed is:

1. A method, comprising:
sensing a time of beat sequence of a patient's heart;
processing the time of beat sequence with a medical device to identify a change in heart rate of a patient from a first heart rate to a second heart rate;
determining with the medical device a ratio of the second heart rate to the first heart rate;
continuously updating the first heart rate;
autonomously determining with the medical device a first dynamic ratio threshold for the ratio based on a first patient activity and a second dynamic ratio threshold for the ratio based on a second patient activity;
autonomously determining with the medical device a current dynamic ratio threshold for the ratio which is within a range between the first dynamic ratio threshold and the second dynamic ratio threshold, wherein the current dynamic ratio threshold is based upon a most recently updated window of the first heart rate;
comparing the ratio to the current dynamic ratio threshold; and
detecting a neurologic event based on an occurrence of the ratio exceeding the current dynamic ratio threshold.

2. The method of claim 1, wherein the current dynamic ratio threshold decreases as the first heart rate increases.

3. The method of claim 1, wherein the neurologic event is an epileptic seizure.

4. The method of claim 1, further comprising:
initiating at least one responsive action selected from: logging at least one of a neurological event occurrence, a time of occurrence of the neurological event, or a severity measure of the neurological event; issuing a warning of the neurological event; issuing an alarm; initiating a responsive therapy to treat the neurologic event; and sending an email to at least one of the patient, a caregiver, a responder, and a physician.

5. The method of claim 4, wherein the responsive therapy comprises applying an electrical signal to at least one cranial nerve selected from a vagus nerve, a trigeminal nerve, a glossopharyngeal nerve, a hypoglossal nerve, and branches of the foregoing.

6. The method of claim 1, wherein:
the second heart rate comprises a first statistical measure of central tendency in a short-term window ending in a present time; and
the first heart rate comprises a second statistical measure of central tendency in a time window beginning prior to a start of the short-term window from which the second heart rate is determined.

7. The method of claim 1, wherein determining the current dynamic ratio threshold is further based on the first heart rate and a maximum heart rate of the patient.

8. The method of claim 1, wherein determining the current dynamic ratio threshold is further based on the first heart rate and a resting heart rate of the patient.

9. An article of manufacture comprising a computer-readable non-transitory storage medium having programming configured to cause processing circuitry to perform processing including:
sensing a time of beat sequence of a patient's heart;
processing the time of beat sequence with a medical device to identify a change in heart rate of a patient from a first heart rate to a second heart rate;
continuously updating the first heart rate;
determining with the medical device a ratio of the second heart rate to the first heart rate;
autonomously determining with the medical device a first dynamic ratio threshold for the ratio based on a first patient activity and a second dynamic ratio threshold for the ratio based on a second patient activity;
autonomously determining with the medical device a current dynamic ratio threshold for the ratio which is within a range between the first dynamic ratio threshold and the second dynamic ratio threshold, wherein the current dynamic ratio threshold is based upon a most recently updated window of the first heart rate;
comparing the ratio to the current dynamic ratio threshold; and
detecting a neurologic event based on an occurrence of the ratio exceeding the current dynamic ratio threshold.

10. The article of claim 9, wherein the current dynamic ratio threshold decreases as the first heart rate increases.

11. The article of claim 9, wherein the neurologic event is an epileptic seizure.

12. The article of claim 9, wherein the first heart rate is a background heart rate and the second heart rate is a foreground heart rate.

13. An apparatus, comprising:
at least one sensor configured to sense a time of beat sequence of a patient's heart;
a medical device comprising:
a) a heart rate determination module configured to identify from the time of beat sequence a change in heart rate of a patient from a first heart rate to a second heart rate, and continuously update the first heart rate;
b) a parameter determination module configured to determine a ratio of the second heart rate to the first heart rate;
c) a dynamic threshold determination module configured to autonomously determine a first dynamic ratio threshold for the ratio based on a first patient activity and a second dynamic ratio threshold for the ratio based on a second patient activity, the dynamic threshold determination module configured to autonomously determining with the medical device a current dynamic ratio threshold for the ratio which is within a range between the first dynamic ratio threshold and the second dynamic ratio threshold, wherein the current dynamic ratio threshold is based upon a most recently updated window of the first heart rate; and d) a comparison module configured to compare the ratio to the current dynamic ratio threshold; and
e) a neurologic event detection module configured to detect a neurologic event based on an occurrence of the ratio exceeding the current dynamic ratio threshold.

14. The apparatus of claim 13, wherein the current dynamic ratio threshold determined by the dynamic threshold determination module decreases as the first heart rate increases.

15. The apparatus of claim 13, wherein the at least one sensor and the medical device are configured to be implanted in the patient.

* * * * *